US006514939B1

(12) United States Patent
Shimkets

(10) Patent No.: US 6,514,939 B1
(45) Date of Patent: Feb. 4, 2003

(54) ATRIAL NATRIURETIC FACTOR MUTANTS AND ISCHEMIC STROKE

(75) Inventor: Richard August Shimkets, West Haven, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/428,929

(22) Filed: Oct. 28, 1999

Related U.S. Application Data

(63) Continuation of application No. 08/916,043, filed on Aug. 21, 1997, now Pat. No. 6,013,630.

(51) Int. Cl.$^7$ .......................... A61K 38/00; C07K 14/47
(52) U.S. Cl. .......................... 514/12; 530/324; 530/350
(58) Field of Search .................. 530/350, 324; 514/12

(56) References Cited

U.S. PATENT DOCUMENTS

| 5,212,286 A | * | 5/1993 | Lewicki et al. ............. 530/324 |
| 5,665,704 A | * | 9/1997 | Lowe et al. | |
| 6,013,630 A | | 1/2000 | Shimkets ...................... 514/12 |

FOREIGN PATENT DOCUMENTS

| WO | WO 95/13296 | 5/1995 |
| WO | PCT/US97/15690 | 1/1997 |

OTHER PUBLICATIONS

Hancock, 1995 "Chapter X Ischemic Heart Disease: Acute Myocardial Infarction" In: Scientific American Medicine, Dale and Federman (eds.), Scientific American, Inc., New York, pp. 1–28.
Song, et al. 1989 Development of more potent atrial natriuretic factor (ANF) analogs. Eur. J. Pharm. 160: 141–148.
"STROKE" Dorland and Newman (ed.), Dorland's Illustrated Medical Dictionary 28$^{th}$ Edition, W.B. Saunders Company, Philadelphia, PA, (1994) 1591.
Barnett, 1988, "Cerebral ischemia and infarction" *Cecil Textbook of Medicine* (W.b. Saunders Co., Philadelphia) pp. 2162–2173.
Boers et al., 1985, "Heterozygosity for homocystinuria in premature peripheral and cerebral occlusive arterial disease", N. Eng. J. Med. 313:709–715.
Brass et al., 1991, "A study of twins and stroke", Stroke 23:221–223.
Calabresisi et al., 1970, "Effects of treatment on morbidity in hypertension", JAMA 213:1143–1152.
Chang et al., 1996, "Natriuretic peptide receptors on human trabecular meshwork cells", Curr. Eye Res. 15:137–143.
de leon et al., 1994, "Rat renal preglomerular vessels, glomeruli and papillae do not express detectable quantities of B–type natriuretic peptide receptor", J. Hypertens. 12:539–548.

DeFaire et al., 1975, "concordance for mortality with special reference to ischemic heart disease and cerebrovascular disease", Prev. Med. 4:509–517.
Estrada et al., 1994, "High plasma levels of endothelial–1 and atrial natriuretic peptide in patients with acute ischemic stroke", Am. J. Hypertens. 7:1085–1089.
Garcia et al., 1989, "Glomerular atrial natriuretic factor receptors in spontaneously hypertensive rats", Hypertension 13:567–574.
GenBank M30262, "Human cardiodilatin–atrial natriuretic factor (CDD–ANF) mRNA, complete cds" reported in Nakayama et al, 1984 Nature 310: 699–701.
GenBank Accession No. K02062, K02063, "Rat PND gene encoding atrial natriuretic factor, complete cds." compilation sequence reported in Dennedy et al 1984 Biochem. Biophys. Res. Commun 122:1076–1082, et seq.
He et al., 1995, "High–yield affinity alkylation of the atrial natriuretic factor receptor binding site", Bioconjugate Chen. 6:541–548.
Hutter, 1995, "Ischemic heart disease: Angina pectoris" *Scientific American: Medicine, vol. 1* (Scientific American, Inc., New York) Chapter 1 pp. 1–19.
Iwashina et al., 1994, "His$^{145}$ —Trp$^{146}$ residues and the disulfide–linked loops in atrial natriuretic peptide receptor are critical for the ligand–binding activity", J. Biochem. 115:563–567.
Jeffs et al., 1997, "Sensitivity to cerebral ischemic insult in a rat model of stroke is determined by a single genetic locus", Nat. Gen. 16:364–367.
Kannel et al., 1970, "Epidemiologic assessment of the role of blood pressure in stroke", JAMA 214:301–120.
Levy et al., 1990, "Mutation ofthe Alzheimer's disease amyloid gene in hereditary cerebral hemorrhage, Dutch type", Science 248:1124–1126.

(List continued on next page.)

*Primary Examiner*—Marianne P. Allen
(74) *Attorney, Agent, or Firm*—Mintz Levin; Naomi S. Biswas; Ivor R. Elrifi

(57) ABSTRACT

The present invention is based upon the observation that a mutant atrial natriuretic factor (ANF) gene increases stroke latency in spontaneously hypertensive rats-stroke prone (SHRSP). Accordingly, the present invention provides methods using mutant ANF proteins, fragments, analogs, derivatives and homologs of mutant ANF proteins, the nucleic acids encoding these mutant ANF proteins, as well as modulators of ANF for treating or preventing ischemic diseases, in particular ischemic stroke. The invention also relates to methods of diagnosis, prognosis and screening for a disposition for diseases and disorders associated with increased levels of ANF. Pharmaceutical compositions, methods of screening for ANF mutants and ANF modulators with utility for treatment and prevention of ischemic stroke are also provided.

18 Claims, 10 Drawing Sheets

OTHER PUBLICATIONS

Figure 1A:
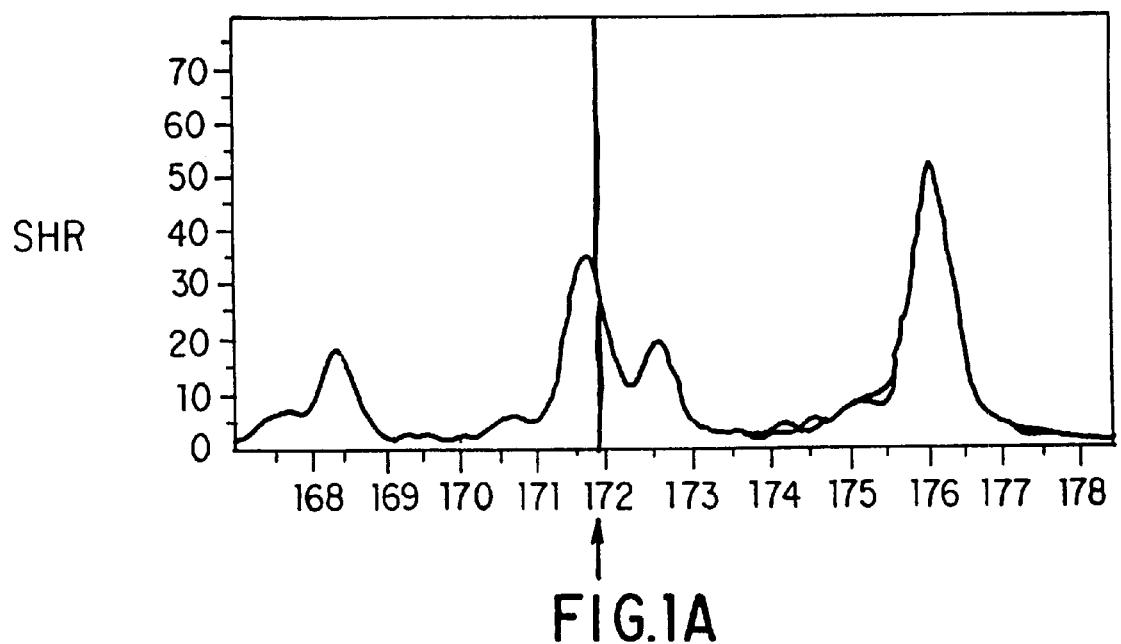
Figure 1B:
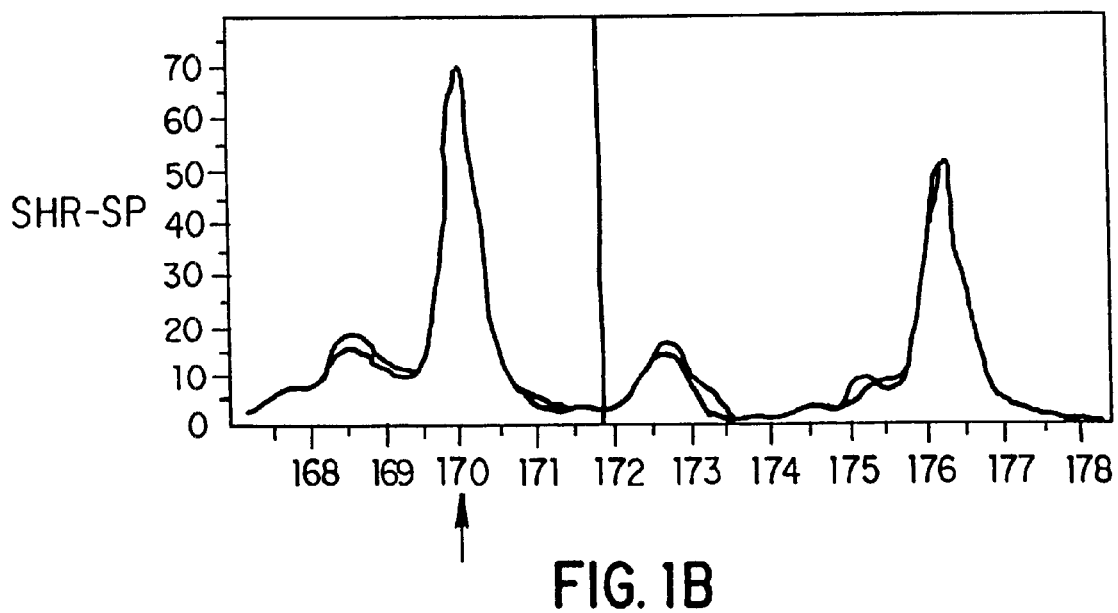

Miao et al., 1995, "Mutational inactivation of the catalytic domain of guanylate cyclase–A receptor", Hypertension 25:694–698.

Nascimenato–Gomes et al., 1995, "Atrial natriuretic peptide modulates the effect of angiotensin II on the concentration of free calcium in the sytosol of Mandin–Darby canine kidney cells", Brazil, J. of Med. & Biol. Res. 28:609–613.

Needleman et al., 1989, "The biochemical pharmacology of atrial peptides", Ann. Rev. Pharmacol. Toxicol. 29:23–54.

Palsdottir et al., 1988, "Mutation in systatin c gene causes heredity brai nhaemorrhage", Lancet 2:603–604.

Rubattu et al., "Chromosomal mapping of quantitative train loci contributing to stroke in a rat model of complex human disease", Nat. Gen. 13:429–434.

Schulz et al., 1989, "the primary structure of a plasma membrance guanylate cyclase demonstrates diversity within this new receptor family" Cell 58:1155–1162.

Vesely et al., 1996, "Atrial natriuretic peptide increases adrenomedullin in the circulation of healthy humans", Life Sciences 59:243–254.

Vesely et al., 1996, "Atrial natriuretic peptides negatively and positively modulate circulating endothelin in humans", Metabolish: Clinical & Experimental 45:315–319.

Vesely et al., 1992, "Specific binding site for pro atrial natriuretic factors 1–30, 31–67, and 99–126 on distal nephrons, proximal tubules, renal cortical and medullary membranes", Renal Rhys. & Biochem. 15:23–32.

Vesely et al., 1995, "Atrial natriuretic peptides and cyclic guanosine monophosphate metabolism", Amer. J. Med. Sci. 310:143–149.

Yatsu et al., 1997, "Cerebrovascular disorders" *Scientific American: Medicine, vol. 3* (Scientic American, Inc., New York) Chapter 11 pp. 1–12.

Veterans Administration Cooperative Study Group on Antihypertensive Agents, 1970. "Effects of treatment on morbidity in hypertension. II. Results in patients with diastolic blood pressure averaging 90 through 114 mm Hg." JAMA. 213: 1143–1152.

Okayama, et al., 1989. "Rapid, nonradioactive detection of mutations in the human genome by allelespecific amplification." J Lab Clin Med. 114: 105–113.

Reuters Health Information. 1998. "Gene mutation may double stroke risk." MedScape News Headlines, Sep. 23, 1998. URL:http://www.medscape.com/reuters/thu/t0923–4f.html.

Rubattu, et al., 1998. "Identification of a genetic determinant of stroke, the gene encoding the atrial natriuretic peptide (ANP)." Conference Abstract: Impact of Rat Genome Mapping on Biomedical Research, Oct. 4–6, 1998. Medical School Hannover, Lower Saxony, Germany. pg V/3.

Shilo, et al., 1981. "DNA sequences homologous to vertebrate oncogenes are conserved in *Drosophila melanogaster*." Proc Natl Acad Sci USA. 78: 6789–6792.

Sommer, et al., 1992. "PCR amplification of specific alleles (PASA) is a general method for rapidly detecting known single–base changes." BioTechniques. 12:82–87.

Vesely, et al., 1996. "Atrial natriuretic peptides negatively and positively modulate circulating endothelin in humans." Metabolism: Clin & Exp. 45: 315–319.

* cited by examiner

Gly Pro Trp Asp Pro Ser Asp Arg Ser Ala Leu Leu Lys Ser Lys Leu
 1           5                   10                  15

Arg Ala Leu Leu Ala Gly Pro Arg Ser Leu Arg Arg
         20                  25

FIG.2

Met Gly Ser Phe Ser Ile Thr Lys Gly Phe Phe Leu Phe Leu Ala Phe
1              5                   10                15

Trp Leu Pro Gly His Ile Gly Ala Asn Pro Val Tyr Ser Ala Val Ser
            20                  25                30

Asn Thr Asp Leu Met Asp Phe Lys Asn Leu Leu Asp His Leu Glu Glu
            35                  40                  45

Lys Met Pro Val Glu Asp Val Met Pro Pro Gln Ala Leu Ser Glu
    50                  55                  60

Gln Thr Asp Glu Ala Gly Ala Ala Leu Ser Ser Leu Ser Glu Val Pro
65              70                  75                      80

Pro Trp Thr Gly Glu Val Asn Pro Ser Gln Arg Asp Gly Gly Ala Leu
                85                  90                  95

Gly Arg Gly Pro Trp Asp Pro Ser Asp Arg Ser Ala Leu Leu Lys Ser
            100                 105                 110

Lys Leu Arg Ala Leu Leu Ala Gly Pro Arg Ser Leu Arg Arg Ser Ser
            115                 120                 125

Cys Phe Gly Gly Arg Ile Asp Arg Ile Gly Ala Gln Ser Gly Leu Gly
    130                 135                 140

Cys Asn Ser Phe Arg Tyr Arg Arg
145             150

FIG. 3

```
GAATTCTTTA GAGCCTGTAT CATGTTGGCT TCCTGGCTGA CTTCATACTC TAAAAAAATA  60
TAATAGCTCT TTCACCTGAC TGCTAACAGG GACATCTAGG GTGGGGGTGG GCTGTCTGGG 120
GCCAGAGGTC CACCCACGAG GCCAATGAAT CAGGTGTGAA GGTAACTCCA GTATGCGGGC 180
TCCCCCGCAG CCTAGCTGTC TCCCAGCTGC CTGTCATTGC CTCTCCTCCC GCCCTTATTT 240
GGAGCCCCTG ACAGCTGAGA TGCAAGCAGA GGGAGCTGGG TGTGGGCCAG CCGTCACCCT 300
CTGCTTCCCT GCATGGGTCC CGTTGCCAGG GAGAAGGAAT CCTGAGGCGA GCGCCCAGGA 360
AGATAACCAA GGACTCTTTT CTGCTCTTCT CACACCTTTG AAGTGGGGGC CTCTTGAGGC 420
AAATCATCAA GAATGTGACT CTTGCAGCTG AGGGTCTGGG GGAGGGAGGG TTACTGGAGC 480
TGCTCAAGGC AAAGGGGCTG TGACAAGCTT CGCTGGACTG ATAACTTTAA AAGGGCATCT 540
TCTGCTGGCC GCCGCAAGTG ACAGAATGGG GAGGGTTCCA GCTCTCCTGC GTTCTCAGGG 600
AGCTGGGGGG CTATAAAAAC GGGAGACGCC GGGCAGCTGG GAGACAGTGA CGGACAAAGG 660
CTGAGAGAGA AACCAGAGAG TGAGCCGAGA CAGCAAACAT CAGATCGTGC CCCGACCCAC 720
GCCAGC ATG GGC TCC TTC TCC ATC ACC AAG GGC TTC TTC CTC TTC CTG    768
       Met Gly Ser Phe Ser Ile Thr Lys Gly Phe Phe Leu Phe Leu
       1               5                   10

GCC TTT TGG CTC CCA GGC CAT ATT GGA GCA AAT CCC GTA TAC AGT GCG  816
Ala Phe Trp Leu Pro Gly His Ile Gly Ala Asn Pro Val Tyr Ser Ala
15              20                  25                  30

GTG TCC AAC ACA GAT CTG ATG GAT TTC AAG GTAGGGCCAG GAAGTGGGGC    866
Val Ser Asn Thr Asp Leu Met Asp Phe Lys
                35                  40

ATGGACTGGG ACCAGGGTCT CCTTGGTACT GGGTCCATTC CTGAGACATC CCCCTTTCTC 926

TGCATTTATT TTCCCCTGAT AAAG AAC CTG CTA GAC CAC CTG GAG GAG AAG   977
                          Asn Leu Leu Asp His Leu Glu Glu Lys
                                       45
ATG CCG GTA GAA GAT GAG GTC ATG CCT CCG CAG GCC CTG AGC GAG CAG 1025
Met Pro Val Glu Asp Glu Val Met Pro Pro Gln Ala Leu Ser Glu Gln
50              55                  60                  65

ACC GAT GAA GCG GGG GCG GCA CTT AGC TCC CTC TCT GAG GTG CCT CCC 1073
Thr Asp Glu Ala Gly Ala Ala Leu Ser Ser Leu Ser Glu Val Pro Pro
                70                  75                  80

TGG ACT GGG GAA GTC AAC CCG TCT CAG AGA GAT GGA GGT GCT CTC GGG 1121
Trp Thr Gly Glu Val Asn Pro Ser Gln Arg Asp Gly Gly Ala Leu Gly
                85                  90                  95

CGC GGC CCC TGG GAC CCC TCC GAT AGA TCT GCC CTC TTG AAA AGC AAA 1169
Arg Gly Pro Trp Asp Pro Ser Asp Arg Ser Ala Leu Leu Lys Ser Lys
            100                 105                 110

CTG AGG GCT CTG CTC GCT GGC CCT CGG AGC CTG CGA AGG TCA AGC TGC 1217
Leu Arg Ala Leu Leu Ala Gly Pro Arg Ser Leu Arg Arg Ser Ser Cys
        115                 120                 125
```

FIG. 4A

```
TTC GGG GGT AGG ATT GAC AGG ATT GGA GCC CAG AGC GGA CTA GGC TGC    1265
Phe Gly Gly Arg Ile Asp Arg Ile Gly Ala Gln Ser Gly Leu Gly Cys
130             135             140             145

AAC AGC TTC CGG GTAAGAGGCG CTGCGGGTGA AACGGGATAG AGGCCAGGTG        1317
Asn Ser Phe Arg

GGGTCTTGTT AGGGCTCCGA CCTTGCCAAG GACTAGTGCC AGTCTGCATC TTCGGCAGTA  1377

CAGAGTCCAG TGCGTGAGTC TTATGTTCTC TGAGAGTTCT GCCCCACCCT-GATGGGTGTC 1437

CCTTGAGTTT CAAGAGAATG ACAGCAGCTG CTGCAGGATC TGAGCCACGA GCACTGGGAA 1497

ATTAGAATAC AGGGCCAAGA CCGCCCACAT TAACGCTTAC CGGCGCCCTG TTTGCCAGTT 1557

TACCGAAGAG GCCAGACTGT GGCTGGTGGG AAAGAGTTGG TCACTGGTCA GGTTAACAG  1617

GTTAGCCCAG TGAAGGTAGA TCATCAGAACC GATTTATTTT TCTCTTTGTA G TAC CGA 1674
                                                        Tyr Arg
                                                        150
AGA TAA CAGCCAAATC TGCTCGAGCA GATCGCAAAA GATCCCAAGC CTTGCGGTGT    1730
Arg *

GTCACACAGC TTGGTCGCAT TGCCACTGAG AGGTGGTGAA TACCCTCCTG GAGCTGCAGC 1790

TTCCTGTCTT CATCTATCAC GATCGATGTT AAGTGTAGAT GAGTGGTTTA GTGAGGCCTT 1850

ACCTCTCCCA CTCTGCATAT TAAGGTAGAT CCTCACCCCT TTCAGAAAGC AGTTGGAAAA 1910

AAATAAATCC GAATAAACTT CAGCACCACG GACAGACGCT GAGGCCTGGC TGCGGTTCTT 1970

TGGCTCCTTT CTGTCACCAG TTCCTTGCGG TCCACAACCT TGATCTTTCG TTTCTCCCTC 2030

CTTCCCTCCT TCTTCTTGCT GGGCGTGTGT GTGTGTGTGT GTGATGGTGT GTGTGTGTGT 2090

GTGTGTGTGT GTGTGTGTGT GTGTGTGTGT GTGTGTGTGT TGGTGAGGGG GTCACACTAT 2150

GGCCCTCAAC ATGCTCTGCC TCCATTGCAG AACCCTGAAA AGCTCGCCCA GACTGAAAAG 2210

GGCATTTATT TTTAATTACC TTTAAAATAC CTTTTCCTGA GGACAGAGGC AATGATACGT 2270

ATGCTTAGTT TCACGAATCC CTCTCACTGT CTGGCTACAG CCTGGGTGGC TTTAAGGGGC 2330

ATTTGAGAGG ACCAGGGACT ATCCAGATCT                                  2360
```

FIG. 4B

Gly Pro Trp Asp Ser Ser Asp Arg Ser Ala Leu Leu Lys Ser Lys Leu
 1               5                   10                  15

Arg Ala Leu Leu Thr Ala Pro Arg Ser Leu Arg Arg
           20                  25

FIG. 5

```
Met Ser Ser Phe Ser Thr Thr Thr Val Ser Phe Leu Leu Leu Leu Ala
 1           5                   10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
            35                  40                  45

Glu Lys Met Pro Leu Glu Asp Glu Val Val Pro Pro Gln Val Leu Ser
            50                  55                  60

Glu Pro Asn Glu Glu Ala Gly Ala Ala Leu Ser Pro Leu Pro Glu Val
 65                  70                  75                  80

Pro Pro Trp Thr Gly Glu Val Ser Pro Ala Gln Arg Asp Gly Gly Ala
                85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
            115                 120                 125

Ser Cys Phe Gly Gly Arg Met Asp Arg Ile Gly Ala Gln Ser Gly Leu
    130                 135                 140

Gly Cys Asn Ser Phe Arg Tyr
145             150
```

FIG. 6

```
TGGCGAGGGA CAGACGTAGG CCAAGAGAGG GGAACCAGAG AGGAACCAGA GGGGAGAGAC   60
AGAGCAGCAA GCAGTGGATT GCTCCTTGAC GACGCCAGC ATG AGC TCC TTC TCC    114
                                          Met Ser Ser Phe Ser
                                           1               5

ACC ACC ACC GTG AGC TTC CTC CTT TTA CTG GCA TTC CAG CTC CTA GGT   162
Thr Thr Thr Val Ser Pha Leu Leu Leu Leu Ala Phe Gln Leu Leu Gly
            10                  15                  20

CAG ACC AGA GCT AAT CCC ATG TAC AAT GCC GTG TCC AAC GCA GAC CTG   210
Gln Thr Arg Ala Asn Pro Met Tyr Asn Ala Val Ser Asn Ala Asp Leu
                25                  30                  35
ATG GAT TTC AAG AAT TTG CTG GAC CAT TTG GAA GAA AAG ATG CCT TTA   258
Met Asp Phe Lys Asn Leu Leu Asp His Leu Glu Glu Lys Met Pro Leu
            40                  45                  50

GAA GAT GAG GTC GTG CCC CCA CAA GTG CTC AGT GAG CCG AAT GAA GAA   306
Glu Asp Glu Val Val Pro Pro Gln Val Leu Ser Glu Pro Asn Glu Glu
        55                  60                  65

GCG GGG GCT GCT CTC AGC CCC CTC CCT GAG GTG CCT CCC TGG ACC GGG   354
Ala Gly Ala Ala Leu Ser Pro Leu Pro Glu Val Pro Pro Trp Thr Gly
 70                  75                  80                  85

GAA GTC AGC CCA GCC CAG AGA GAT GGA GGT GCC CTC GGG CGG GGC CCC   402
Glu Val Ser Pro Ala Gln Arg Asp Gly Gly Ala Leu Gly Arg Gly Pro
                90                  95                 100

TGG GAC TCC TCT GAT CGA TCT GCC CTC CTA AAA AGC AAG CTG AGG GCG   450
Trp Asp Ser Ser Asp Arg Ser Ala Leu Leu Lys Ser Lys Leu Arg Ala
            105                 110                 115

CTG CTC ACT GCC CCT CGG AGC CTG CGG AGA TCC AGC TGC TTC GGG GGC   498
Leu Leu Thr Ala Pro Arg Ser Leu Arg Arg Ser Ser Cys Phe Gly Gly
        120                 125                 130

AGG ATG GAC AGG ATT GGA GCC CAG AGC GGA CTG GGC TGT AAC AGC TTC   546
Arg Met Asp Arg Ile Gly Ala Gln Ser Gly Leu Gly Cys Asn Ser Phe
    135                 140                 145

CGG TAC TGA AGATAACAGC CAGGGAGGAC AAGCAGGGCT GGGCCTAGGG           595
Arg Tyr *
150

ACAGACTGCA AGAG GCTCCT GTCCCTGGG GTCTCTGCTG CATTTGTGTC ATCTTGTTGC 655
CATGGAGTTG TGATCATCCC ATCTAAGCTG CAGCTTCCTG TCAACACTTC TCACATCTTA 715
TGCTAACTGT AGATAAAGTG GTTTGATGGT GACTTCCTCG CCTCTCCCAC CCCATGCATT 775
AAATTTTAAG GTAGAACCTC ACCTGTTACT GAAAGTGGTT TGAAAGTGAA TAAACTTCAG 835
CACCATGGAC                                                       845
```

FIG. 7

ATRIAL NATRIURETIC FACTOR MUTANTS AND ISCHEMIC STROKE

RELATED APPLICATION

This application is a continuing application under 37 C.F.R. §1.53(b) of U.S. Ser. No. 08/916,043, now U.S. Pat. No. 6,013,630, Jan. 11, 2000 filed on Aug. 21, 1977, incorporated herein by reference in its entirety.

1. FIELD OF THE INVENTION

This invention relates to mutants of atrial natriuretic factor, particularly mutants of atrial natriuretic factor that are protective for stroke. The invention further relates to methods of treating or preventing stroke by administration of mutants of atrial natriuretic factor. Additionally, the invention relates to methods of diagnosis, prognosis and screening for alleles of the atrial natriuretic factor gene that are protective for stroke.

2. BACKGROUND

Ischemic stroke is a common, complex disorder caused by a combination of genetic and environmental factors that is associated with long term disability and death. Apart from the treatment of hypertension, a risk factor for stroke (Kannel et al., *JAMA* 214:301–310 (1970); Veterans Administration Cooperative Study Group on Antihypertensive Agents, Effects of treatment of morbidity in hypertension, *JAMA* 213:1143–1152 (1970)), few preventative therapeutics are available, and no genetic test for stroke predisposition exists. A significant genetic component to human stroke predisposition has been demonstrated by both rare monogenic inheritance (Palsdottir et al. *Lancet* 2:603–604 (1988); Boers et al., *N. Eng. J. Med.* 313:709–715 (1985); Levy et al., *Science* 248:1124–1126 (1990)) and by increased concordance in monozygotic compared with dizygotic twins (De Faire et al., *Prev. Med.* 4:509–517 (1975); Brass et al. *Stroke* 23:221–223 (1992)).

The spontaneously hypertensive stroke-prone rat (SHRSP) strain is an animal model of ischemic stroke. SHRSP rats suffer cerebrovascular events with 99% penetrance when administered a diet high in sodium to induce hypertension. These SHRSP rats are closely related to the SHR (spontaneously hypertensive rat) strain which develops hypertension, but not ischemic stroke, when administered a high sodium diet. Genetic analysis of the progeny of SHR-SHRSP rat intercrosses revealed that three Quantitative Trait Loci (QTLS) contribute to stroke latency (Rubattu et al., *Nat. Gen.* 13:429–434 (1996)). While a locus on chromosome 1 significantly correlated with the occurrence of stroke, two loci, one on chromosome 4 and another on chromosome 5, were actually associated with increased stroke latency. The chromosome 5 locus mapped near the gene coding for ANF (atrial natriuretic factor) and BNF (brain natriuretic factor). None of the three loci were associated with hypertension.

A second study by Jeffs et al. (*Nat. Gen.* 16:364–367 (1997)) analyzed F2 progeny of intercrosses between the SHRSP animals and a normotensive, non-stroke rat strain Wistar-Kyoto (WKY). A chromosome 5 locus, which also co-localized with ANF and BNF, was implicated in increased infarct susceptibility and severity in the SHRSP rats.

ANF is a small peptide hormone known to have vasoactive and diuretic activities and functions both to relax smooth muscle and to reduce sodium reabsorption and intravascular volume (Needleman et al., *Ann. Rev. Pharmacol. Toxicol.* 29:23–54 (1989)). ANF is derived from the prohormone atrial natriuretic peptide (ANP) which appears to be expressed in response to increased blood volume or sodium levels. The proANP is initially expressed as a single polypeptide chain and is proteolytically processed within the cell into four peptides, all of which have been implicated in the diuretic process of vasodilation: Long Acting Natriuretic Peptide, Vessel Dialator, Kaliuretic Peptide and Atrial Natriuretic Factor (Vesely et al., *Metabolism: Clinical & Experimental* 45: 315–319 (1996)). ANF is derived from amino acids 99–126 of ProANP. The physiological activity of ANF appears to be mediated through binding to the guanylate cyclase-A receptor by increasing secretion of cGMP into plasma and urine (Vesely et al., *Amer. J. Med. Sci.* 310:143–149 (1995); Miao et al., *Hypertension* 25:694–69 (1995)).

Garcia et al. (*Hypertension* 13:567–574 (1989)) previously found that SHR had higher plasma ANF levels, and lower glomerular ANF receptor density, than normotensive controls. Additionally, Estrada et al. (*Am. J. Hypertens.* 7:1085–1089 (1994)) noted that elevated ANF levels have been detected in ischemic stroke patients. However, there has been no suggestion in the art that mutant ANF proteins or modulators (e.g., antagonists, agonists or inhibitors) of ANF would be useful as therapeutics or prophylactics for ischemic stroke.

The present inventors have discovered that the ANF gene in the SHRSP strain has the glycine substituted with a serine residue at position 1 of rat ANF as depicted in FIG. 2 (SEQ ID NO:1) (amino acid 99 of the proANP amino acid sequence as depicted in FIG. 3 (SEQ ID NO:2)). Furthermore, the present inventors have realized that this mutant ANF locus coincides with the chromosomal locus associated with increased stroke latency in the SHRSP animals. Accordingly, the ANF mutants and mutant ANF alleles described herein are useful in the treatment and prevention of ischemic stroke, and screening for a genetic predisposition for protection against ischemic stroke.

Citation or discussion of a reference herein shall not be construed as an admission that such is prior art to the present invention.

3. SUMMARY OF THE INVENTION

The present invention relates to mutants of ANF, preferably mutants of ANF and ANF derivatives, homologs, and fragments, preferably ANF mutants having one or more substitutions of amino acid residues and that binds to an anti-ANF antibody, more preferably an ANF mutant with a mutation at amino acid position 1 (of the rat or human ANF sequences as depicted in FIGS. 2 and 5, respectively (SEQ ID NOS:1 and 4, respectively)), most preferably where the mutation at position 1 of ANF is a substitution of the glycine residue with a serine.

The present invention further provides methods of treating or preventing stroke or ischemic disease, preferably ischemic stroke. In one embodiment, stroke or ischemic disease is treated or prevented by administration of a mutant ANF or a derivative, fragment or homolog thereof, preferably ANF mutants having one or more substitutions of amino acid residues and that bind to an anti-ANF antibody, more preferably an ANF mutant with a mutation at amino acid position 1 (of the rat ANF sequence as depicted in FIG. 2; SEQ ID NO:1), most preferably where the mutation at position 1 of ANF is a substitution of the glycine residue with a serine. Pharmaceutical compositions are also provided.

Also provided are methods of diagnosis, prognosis, and screening by detecting mutant ANF proteins and/or nucleic acids. In a preferred embodiment, an allele protective against stroke is screened for by detecting the presence of a mutation in the ANF gene or protein. Specific oligonucleotides that can be used to detect these mutant alleles are provided. Diagnostic, prognostic and screening kits are also provided.

In another aspect of the invention, assays for screening for ANF mutants that are protective for stroke are provided. Additionally, the invention also includes methods of screening for modulators of ANF activity that affect stroke latency or stroke severity.

3.1. Definitions

| | |
|---|---|
| ANF | Atrial Natriuretic Factor |
| QEA ™ | Quantitative Expression Analysis |
| SHR | Spontaneously Hypertensive Rat |
| SHRSP | Spontaneously Hypertensive Rat Stroke-Prone |
| WKY | Wistar-Kyoto (Rat) |

4. DESCRIPTION OF THE FIGURES

FIGS. 1A–F. Panels A and B depict the profiles of the QEA™ labeled products in whole hearts from SHR (A) and SHR-SP (B) rats, with each trace representing results from an individual heart. The arrow below the X-axis indicates the position for ANF. Panels B and C show a comparison of the profiles for the QEAW reactions for the SHR (C) and SHR-SP (D) hearts performed in the presence (lower trace) or absence (upper trace) of the "poisoning" oligonucleotide specific for the ANF gene. These profiles in panels A–D are depicted as the relative scaled intensity of the fluorescent label (on the Y-axis) versus the number of nucleotide bases (on the X-axis). Panels E and F present the output from the automatic DNA sequencing of the ANF nucleotide sequence complementary to the sequence coding for the mutation at amino acid 1 of ANF. Panel E shows that portion of the ANF nucleotide sequence from SHR rats; Panel F shows that portion of the ANF nucleotide sequence from SHRSP rats. The position of the nucleotide substitution is indicated by an arrow.

FIG. 2. The amino acid sequence of wild type rat ANF (SEQ ID NO:1) (Genbank Accession No. K02062 and K02063 (1986)).

FIG. 3. The amino acid sequence of wild type rat proANP (SEQ ID NO:2) (Genbank Accession No. K02062 and K02063 (1986)).

FIG. 4. The nucleotide sequence of wild type rat proANP (SEQ ID NO:3) with the amino acid sequence indicated for the coding sequences (Genbank Accession No. K02062 and K02063 (1986)).

FIG. 5. The amino acid sequence of human ANF (SEQ ID NO:4) (Genbank Accession No. M30262 (1990)).

FIG. 6. The amino acid sequence of human proANP (SEQ ID NO:5) (Genbank Accession No. M30262 (1990)).

FIG. 7. The nucleotide sequence of human proANP (SEQ ID NO:6) with the amino acid sequence indicated for the coding sequences (Genbank Accession No. M30262 (1990)). The ANF sequence is amino acid residue numbers 100–127 (with amino acid number 100 corresponding to amino acid position 1 of rat ANF).

5. DETAILED DESCRIPTION OF THE INVENTION

The present inventors have discovered that the ANF gene in hypertensive stroke-prone rats (SHRSP), an experimental animal model for stroke, has an amino acid substitution as compared to the ANF gene in spontaneously hypertensive rats (SHR) and wild type rats. The inventors have correlated the NF gene with the major QTL (Quantitative Trait Locus) identified on chromosome 5 in SHRSP as a "protective locus" for stroke, i.e., presence of the QTL increases stroke latency. Sequence analysis of the ANF mRNA in SHRSP and comparison with ANF sequences obtained from sequence databases and from SHR revealed that the SHRSP ANF mutant gene encodes an ANF-protein that has an amino acid substitution of serine for the glycine at position 1 of the rat ANF amino acid sequence as depicted in FIG. 2 (SEQ ID NO:1). The glycine at amino acid 1 of ANF (amino acid 99 of proANP) is conserved among rat, pig, horse and human sequences.

Accordingly, the invention relates to mutants of the ANF protein, as well as derivatives, fragments and homologs thereof, and ANF nucleic acids encoding them, that increase latency to stroke, e.g., in stroke prone rats fed a high salt diet. Preferably, the ANF mutants bind to anti-(wild type) ANF antibodies. In particular, the invention relates to mutant ANFs having one or more substitutions of amino acid residues, preferably a mutant ANF that has an amino acid substitution at or corresponding to amino acid position 1 of rat or human ANF as depicted in FIGS. 2 and 5 (SEQ ID NOS:1 and 4) (or amino acid position 99 of rat proANP as depicted in FIG. 3 (SEQ ID NO:2) or amino acid position 100 or human proANP as depicted in FIG. 6 (SEQ ID NO:5)), in particular a substitution of serine for the glycine at or corresponding to position 1 of rat or human ANF.

One embodiment of the invention provides methods of treatment and prevention of stroke by administration of a mutant ANF protein, or a derivative, fragment or homolog thereof, as provided by the invention. In a preferred embodiment, the mutant ANF, or derivative, fragment or homolog thereof, has an amino acid substitution at or corresponding to amino acid position 1 of rat or human ANF as depicted in FIGS. 2 and 5, respectively (SEQ ID NOS:1 and 4, respectively), in particular, a substitution of serine for the glycine at or corresponding to position 1 of rat or human ANF. Pharmaceutical compositions are also provided.

Another aspect of the invention relates to methods of diagnosis, prognosis and screening for stroke by detecting mutant ANF protein or mRNA. In one embodiment, subjects are screened for a mutant ANF allele protective against stroke.

The present invention also relates to methods of assaying ANF mutants for the ability to affect the predisposition to or onset of stroke and to methods of screening for ANF modulators (i.e. agonists, antagonists and inhibitors of ANF).

5.1. ANF Mutants

ANF mutant proteins, and mutants of derivatives, fragments, homologs and analogs of ANF proteins and the nucleic acids encoding the ANF mutants, protein derivatives and protein analogs are provided by the invention. The ANF mutants of the invention can be ANF proteins having substitutions, deletions or insertions of one, two, three, or more amino acid residues in the wild type ANF protein. Preferably, the ANF mutants bind to an anti-ANF antibody. In one embodiment, the mutant ANF has one or more substitutions of amino acid residues relative to the wild type ANF protein, preferably, one or more amino acid substitutions in the amino acid residues (or in the amino acid residues corresponding to the amino acid residues) selected from among amino terminal residues 1–25, 1–20, 1–15, 1–10, 1–5 or 1–2 of ANF as depicted in FIGS. 2 or 5 (SEQ ID NOS: 1 and 4, respectively). In a preferred embodiment, the mutant ANF has an amino acid substitution at amino acid position 1 of the rat ANF sequence provided in FIG. 2 (SEQ ID NO:1) or the corresponding position (i.e., as identified by aligning the amino acids having sequence identity between or among the rat ANF amino acid sequence and the amino acid-sequence(s) of ANF proteins of other species) of the ANF protein of another species (e.g., amino acid position 1 of human ANF as depicted in FIG. 5 (SEQ ID NO:4)). In a more preferred embodiment, the amino acid at amino acid 1 of rat or human ANF as. depicted in FIGS. 2 and 5, respectively (SEQ ID NOS:1 and 4, respectively), or the at the corresponding amino acid position in a non-rat ANF protein, is substituted with a residue that provides a substrate for kinase activity, e.g. a substitution with a residue from the group consisting of serine, threonine and tyrosine, preferably substitution with a serine residue. In a preferred embodiment, the ANF mutant is a human ANF mutant having amino acid substitutions as its only mutations and that binds an anti-ANF antibody.

In another embodiment, the ANF mutant increases latency to stroke in stroke prone rats (e.g. rats having the stroke predisposing locus of chromosome 1) fed a high salt diet (for example, but not limited to, a diet of 17.5% protein, 3.7 mg/g $Na^+$, 6.3 mg/kg $K^+$, and 0.03 mg/g methionine and 1% NaCl drinking water).

In a specific embodiment of the invention, proteins consisting of or comprising a fragment of an ANF protein or mutant protein consisting of at least 10 (continuous) amino acids of the ANF protein are provided. In other embodiments, the fragment consists of at least 15 or 20 or 25 amino acids of the ANF protein. In a preferred embodiment, the ANF fragment contains the portion of a mutant ANF having the mutation at or corresponding to amino acid position 1 of the amino acid sequence of rat or human ANF as depicted in FIGS. 2 or 5, respectively (SEQ ID NOS:1 or 4, respectively), more preferably with a serine residue substituted for the glycine at position 1.

Derivatives or analogs of ANF include but are not limited to those molecules comprising regions that are substantially homologous to ANF or mutant ANF or fragments thereof (e.g., in various embodiments, at least 60% or 70% or 80% or 90% or 95% identity over an amino acid sequence of identical size or when compared to an aligned sequence in which the alignment is done by a computer homology program known in the art) or whose encoding nucleic acid is capable of hybridizing to a coding AWF sequence, under stringent, moderately stringent, or nonstringent conditions.

The ANF mutants, as well as fragments, derivatives, homologs and analogs ANF mutants, of the invention can be produced by various methods known in the art. The manipulations which result in their production can occur at the gene or protein level. For example, the cloned ANF gene sequence (e.g. as described in Section 5.2 infra) can be modified by any of numerous strategies known in the art (Sambrook et al., 1990, Molecular Cloning, A Laboratory Manual, 2d ed., Cold spring Harbor Laboratory, Cold Spring Harbor, N.Y.). The sequence can be cleaved at appropriate sites with restriction endonuclease(s), followed by further enzymatic modification if desired, isolated, and ligated in vitro. In the production of the gene encoding a mutant, derivative or analog of ANF, care should be taken to ensure that the modified gene remains within the same translational reading frame as ANF, uninterrupted by translational stop signals, in the gene region where the desired ANF activity is encoded.

The ANF-encoding nucleic acid sequence can be mutated in vitro or in vivo, to make changes in the coding regions (e.g. amino acid substitutions, additions or deletions) as well as to create and/or destroy translation, initiation, and/or termination sequences, or to form new restriction endonuclease sites or destroy preexisting ones, to facilitate further in vitro modification. Any technique for mutagenesis known in the art can be used, including but not limited to, chemical mutagenesis, in vitro site-directed mutagenesis (Hutchinson, C., et al., 1978, J. Biol. Chem 253:6551), use of TAB® linkers (Pharmacia), etc.

Manipulations of the ANF sequence may also be made at the protein level. Included within the scope of the invention are ANF protein fragments or other derivatives or analogs which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to specific chemical cleavage by cyanogen bromide, trypsin, chymotrypsin, papain, V8 protease, $NaBH_4$; acetylation, formylation, oxidation, reduction; metabolic synthesis in the presence of tunicamycin; etc. Particularly included within the invention are those modifications which reduce the level or activity of ANF.

In addition, ANF mutants, analogs and derivatives can be chemically synthesized. For example, mutant ANF proteins or a portion thereof, which mediate the desired activity in vivo or in vitro, can be synthesized by use of a peptide synthesizer. Furthermore, if desired, nonclassical amino acids or chemical amino acid analogs can be introduced as a substitution or addition into the ANF sequence. Nonclassical amino acids include but are not limited to the D-isomers of the common amino acids, α-amino isobutyric acid, 4-aminobutyric acid, Abu, 2-amino butyric acid, γ-Abu, ε-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

In another embodiment, the ANF derivative is a chimeric, or fusion, protein comprising an ANF protein or fragment thereof (preferably consisting of at least 10 amino acids of the ANF protein or a mutant ANF protein) joined at its amino- or carboxy-terminus via a peptide bond to an amino acid sequence of a different protein. In one embodiment, such a chimeric protein is produced by recombinant expression of a nucleic acid encoding the protein (comprising an ANF-coding sequence joined in-frame to a coding sequence for a different protein). Such a chimeric product can be made by ligating the appropriate nucleic acid sequences, encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer. Chimeric genes comprising portions of ANF or mutant AMF fused to any heterologous protein-encoding sequences may be constructed. A specific embodiment relates to a chimeric protein comprising a fragment of ANF or mutant ANF of at least six amino acids.

Additionally, due to the degeneracy of nucleotide coding sequences, other DNA sequences which encode substantially the same amino acid sequence as a mutant ANF of the invention may be used in the practice of the present invention. The mutant ANF genes of the invention can be obtained by alteration of nucleotide sequences comprising all or portions of ANF gene by the substitution of different codons that encode the desired amino acid. Additionally, one or more codons encoding a functionally equivalent amino acid residue within the sequence may also be substituted, thus producing a silent change. For example, one or more amino acid residues within the sequence can be substituted by another amino acid of a similar polarity which acts as a functional equivalent, resulting in a silent alteration. Substitutes for an amino acid within the sequence may be selected from other members of the class to which the amino acid belongs. For example, the nonpolar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid.

The invention also provides mutant proANP molecules, containing the mutations as described above for mutant ANF molecules.

5.2. ANP-genes and Proteins

ANF proteins and nucleic acids can be obtained by any method known in the art. The ANF amino acid and nucleotide sequences for, inter alia, human, rat, hamster, dog, mouse, bovine, porcine, *Drosophila melanogaster*, Xenopus, horse, and dogfish are available in the public databases (e.g. Genbank). The amino acid sequence for rat ANF, the amino acid sequence for rat ANP, the nucleotide sequence for rat ANP, the amino acid sequence for human ANF, the amino acid sequence for human ANP and the nucleotide sequence for human ANF are provided in FIGS. 2–7, respectively (SEQ ID NOS:1–6, respectively).

Any eukaryotic cell potentially can serve as the nucleic acid source for the isolation of AMF nucleic acids. The nucleic acid sequences encoding ANF can be isolated from vertebrate, mammalian, human, porcine, bovine, feline, avian, equine, canine, as well as additional primate sources, etc. The DNA may be obtained by standard procedures known in the art from cloned DNA (e.g., a DNA "library"), by chemical synthesis, by cDNA cloning, or by the cloning of genomic DNA, or fragments thereof, purified from the desired cell (see, for example, Sambrook et al., 1989, Molecular Cloning, A Laboratory Manual, 2d Ed., Cold Spring Harbor Laboratory Press, Cold Spring Harbor, N.Y.; Glover, D. M. (ed.), 1985, DNA Cloning: A Practical Approach, MRL Press, Ltd., Oxford, U. K. Vol. I, II.) Clones derived from geno-mic DNA may contain regulatory and intron DNA regions in addition to coding regions; clones derived from cDNA will contain only exon sequences. Whatever the source, the gene should be molecularly cloned into a suitable vector for propagation of the gene.

In the molecular cloning of the gene from cDNA, cDNA is generated from totally cellular RNA or mRNA by methods that are well known in the art. The gene may also be obtained from genomic DNA, where DNA fragments are generated (e.g. using restriction enzymes or by mechanical shearing), some of which will encode the desired gene. The linear DNA fragments can then be separated according to size by standard techniques, including but not limited to, agarose and polyacrylamide gel electrophoresis and column chromatography.

Once the DNA fragments are generated, identification of the specific DNA fragment containing all or a portion of the ANF gene may be accomplished in a number of ways.

A preferred method for isolating an ANF gene is by the polymerase chain reaction (PCR), which can be used to amplify the desired ANF sequence in a genomic or cDNA library or from genomic DNA or cDNA that has not been incorporated into a library. Oligonucleotide primers which would hybridize to ANF sequences can be used as primers in PCR. For example, primers having the sequence 5'-GAATTCAGTTCTCTCCTTCCGCT-3' (SEQ ID NO:7) and 5'-CATGCTGGCGTGGGACGGGGCAC-3' (SEQ ID NO:8) can be used to amplify the rat ANF sequence, and primers having the sequence 5'-GGATCCATTTGTCTCGGGCTG-3' (SEQ ID NO:9) and 5'-CTAGATCAATTAGGCCTCCC-3' (SEQ ID NO:10) can be used to amplify the human ANF sequence. The synthetic oligonucleotides may be utilized as primers to amplify by PCR sequences from a source (RNA or DNA), preferably a cDNA library, of potential interest. PCR can be carried out, e.g., by use of a Perkin-Elmer Cetus thermal cycler and Taq polymerase (Gene Amp™). One can choose to synthesize several different degenerate primers for use in the PCR reactions. It is also possible to vary the stringency of hybridization conditions used in priming the PCR reactions, to allow for greater or lesser degrees of nucleotide sequence similarity between the known ANF nucleotide sequence and the nucleic acid of an ANF homolog being isolated. For cross species hybridization, low stringency conditions are preferred. For same species hybridization, moderately stringent conditions are preferred. After successful amplification of a segment of an ANF homolog, that segment may be molecularly cloned and sequenced, and utilized as a probe to isolate a complete cDNA or genomic clone. This, in turn, will permit the determination and isolation of the gene's complete nucleotide sequence. PCR amplification can also be used to detect and quantitate ANF mRNA levels for, e.g. the diagnostic, prognostic and screening methods described Section 5.4 supra.

Additionally, a portion of the ANF (of any species) gene or its specific RNA, or a fragment thereof, can be purified (or an oligonucleotide synthesized) and labeled, the generated DNA fragments may be screened by nucleic acid hybridization to the labeled probe (Benton, W. and Davis, R., 1977, Science 196:180; Grunstein, M. And Hogness, D., 1975, Proc. Natl. Acad. Sci. U.S.A. 72:3961). Those DNA fragments with substantial homology to the probe will hybridize. ANF nucleic acids can be also identified and isolated by expression cloning using, for example, anti-ANF antibodies for selection.

Alternatives to obtaining the ANF DNA by cloning or amplification include, but are not limited to, chemically synthesizing the gene sequence itself from the known ANF sequence or making cDNA to the mRNA which encodes the ANF protein. Other methods are possible and within the scope of the invention. Once a clone has been obtained, its identity can be confirmed by nucleic acid sequencing (by any method well known in the art) and comparison to known ANF sequences. DNA sequence analysis can be performed by any techniques known in the art, including but not limited to the method of Maxam and Gilbert (1980, Meth. Enzymol. 65:499–560), the Sanger dideoxy method (Sanger, F., et al., 1977, Proc. Natl. Acad. Sci. U.S.A. 74:5463), the use of T7 DNA polymerase (Tabor and Richardson, U.S. Pat. No. 4,795,699), use of an automated DNA sequenator (e.g., Applied Biosystems, Foster City, Calif.) or the method described in PCT Publication WO 97/15690.

Nucleic acids which are hybridizable to an ANF nucleic acid (e.g., having sequence SEQ ID NO:3 or 6), or to a nucleic acid encoding an ANF derivative can be isolated, by nucleic acid hybridization under conditions of low, high, or moderate stringency. By way of example and not limitation, procedures using such conditions of low stringency are as follows (see also Shilo and Weinberg, 1981, Proc. Natl. Acad. Sci. USA 78:6789–6792): Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations are carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe is used. Filters are incubated in hybridization mixture for 18–20 h at 40° C., and then washed for 1.5 h at 55° C. in a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography. If necessary, filters are washed for a third time at 65–68° C. and reexposed to film. Other conditions of low stringency which may be used are well known in the art (e.g., as employed for cross-species hybridizations).

By way of example and not limitation, procedures using such conditions of high stringency are as follows: Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 µg/ml denatured salmon sperm DNA. Filters are hybridized for 48 h at 65° C. in prehybridization mixture containing 100 µg/ml denatured salmon sperm DNA and 5–20×10$^6$ cpm of $^{32}$P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 min before autoradiography. Other conditions of high stringency which may be used are well known in the art.

For example, but not limited to, procedures using such conditions of moderate stringency are as follows: Filters containing DNA are pretreated for 6 h at 55° C. in a solution containing 6×SSC, 5×Denhart's solution, 0.5% SDS and 100 µg/ml denatured salmon sperm DNA. Hybridizations are carried out in the same solution and 5–20×10$^6$ cpm $^{32}$P-labeled probe is used. Filters are incubated in hybridization mixture for 18–20 h at 55° C., and then washed twice for 30 minutes at 60° C. in a solution containing 1×SSC and 0.1% SDS. Filters are blotted dry and exposed for autoradiography. Other conditions of moderate stringency which may be used are well-known in the art. Washing of filters is done at 37° C. for 1 h in a solution containing 2×SSC, 0.1% SDS.

Nucleic acids encoding derivatives and analogs of ANF proteins (see Section 5.1), ANF antisense nucleic acids (see Section 5.3.4), and primers that can be used to detect mutant ANF alleles and AMF gene expression are additionally provided. As is readily apparent, as used herein, a "nucleic acid encoding a fragment or portion of an ANF protein" shall be construed as referring to a nucleic acid encoding only the recited fragment or portion of the ANF protein and not the other contiguous portions of the ANF protein as a continuous sequence.

ANF proteins and derivatives, analogs and fragments of ANF proteins can be obtained by any method known in the art, including but not limited to recombinant expression methods, purification from natural sources, and chemical synthesis.

For example, ANF can be obtained by recombinant protein expression techniques. For recombinant expression, the ANF gene or portion thereof is inserted into an appropriate cloning vector for expression in a particular host cell. A large number of vector-host systems known in the art may be used. Possible vectors include, but are not limited to, plasmids or modified viruses, but the vector system must be compatible with the host cell used. Such vectors include, but are not limited to, bacteriophages such as lambda derivatives, or plasmids such as pBR322 or pUC plasmid derivatives or the Bluescript vector (Stratagene). The insertion into a cloning vector can, for example, be accomplished by ligating the DNA fragment into a cloning vector which has complementary cohesive termini. However, if the complementary restriction sites used to fragment the DNA are not present in the cloning vector, the ends of the DNA molecules may be enzymatically modified. Alternatively, any site desired may be produced by ligating nucleotide sequences (linkers) onto the DNA termini; these ligated linkers may comprise specific chemically synthesized oligonucleotides encoding restriction endonuclease recognition sequences. In an alternative method, the cleaved vector and ANF gene may be modified by homopolymeric tailing. Recombinant molecules can be introduced into host cells via transformation, transfection, infection, electroporation, etc., so that many copies of the gene sequence are generated.

In an alternative method, the desired gene may be identified and isolated after insertion into a suitable cloning vector in a "shot gun" approach. Enrichment for the desired gene, for example, by size fractionation, can be done before insertion into the cloning vector.

In specific embodiments, transformation of host cells with recombinant DNA molecules that incorporate the isolated ANF gene, cDNA, or synthesized DNA sequence enables generation of multiple copies of the gene. Thus, the gene may be obtained in large quantities by growing transformants, isolating the recombinant DNA molecules from the transformants and, when necessary, retrieving the inserted gene from the isolated recombinant DNA.

The nucleotide sequence coding for an ANF protein or a functionally active analog or fragment or other derivative thereof, can be inserted into an appropriate expression vector, i.e., a vector which contains the necessary elements for the transcription and translation of the inserted protein-coding sequence. The necessary transcriptional and translational signals can also be supplied by the native ANF gene and/or its flanking regions. A variety of host-vector systems may be utilized to express the protein-coding sequence. These include but are not limited to mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage, DNA, plasmid DNA, or cosmid DNA. The expression elements of vectors vary in their strengths and specificities. Depending on the host-vector system utilized, any one of a number of suitable transcription and translation elements may be used.

Any of the methods previously described for the insertion of DNA fragments into a vector may be used to construct expression vectors containing a chimeric gene consisting of appropriate transcriptional/translational control signals and the protein coding sequences. These methods may include in vitro recombinant DNA and synthetic techniques and in vivo recombinants (genetic recombination). Expression of nucleic acid sequence encoding an ANF protein or peptide fragment may be regulated by a second nucleic acid sequence so that the ANF protein or peptide is expressed in a host transformed with the recombinant DNA molecule. For example, expression of an ANF protein may be controlled by any promoter/enhancer element known in the art. Promoters which may be used to control ANF expression include, but are not limited to, the SV40 early promoter region (Bernoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42); prokaryotic expression vectors such as the β-lactamase promoter (Villa-Kamaroff, et al., 1978, Proc. Natl. Acad. Sci. U.S.A. 75:3727–3731), or the tac promoter (DeBoer, et al., 1983, Proc. Natl. Acad. Sci. U.S.A. 80:21–25); see also "Useful proteins from recombinant bacteria" in Scientific American, 1980, 242:74–94; promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639–646; Ornitz et al., 1986, Cold Spring Harbor Symp. Quant. Biol. 50:399–409; MacDonald, 1987, Hepatology 7:425–515); insulin gene control region which is active in pancreatic beta cells (Hanahan, 1985, Nature 315:115–122), immunoglobulin gene control region which is active in lymphoid cells (Grosschedl et al., 1984, Cell 38:647–658; Adames et al., 1985, Nature 318:533–538; Alexander et al., 1987, Mol. Cell. Biol. 7:1436–1444), mouse mammary tumor virus control region which is active in testicular, breast, lymphoid and mast cells (Leder et al., 1986, Cell 45:485–495), albumin gene control region which is active in liver (Pinkert et al., 1987, Genes and Devel. 1:268–276), alpha-fetoprotein gene control region which is active in liver (Krumlauf et al., 1985, Mol. Cell. Biol. 5:1639–1648; Hammer et al., 1987, Science 235:53–58; alpha 1-antitrypsin gene control region which is active in the liver (Kelsey et al., 1987, Genes and Devel. 1:161–171), beta-globin gene control region which is active in myeloid cells (Mogram et al., 1985, Nature 315:338–340; Kollias et al., 1986, Cell 46:89–94), myelin basic protein gene control region which is active in oligodendrocyte cells in the brain (Readhead et al., 1987, Cell 48:703–712), myosin light chain-2 gene control region which is active in skeletal muscle (Sani, 1985, Nature 314:283–286), and gonadotropic releasing hormone gene control region which is active in the hypothalamus (Mason et al., 1986, Science 234:1372–1378).

For example, a vector can be used that comprises a promoter operably linked to an ANF-encoding nucleic acid, one or more origins of replication, and, optionally, one or more selectable markers (e.g., an antibiotic resistance gene).

In a specific embodiment, an expression construct is made by subcloning an ANF coding sequence into the EcoRI restriction site of each of the three PGEX vectors (Glutathione S-Transferase expression vectors; Smith and Johnson, 1988, Gene 7:31–40). This allows for the expression of the ANF protein product from the subclone in the correct reading frame.

Expression vectors containing ANF gene inserts can be identified by three general approaches: (a) nucleic acid hybridization, (b) presence or absence of "marker" gene functions, and (c) expression of inserted sequences. In the first approach, the presence of an ANF gene inserted in an expression vector can be detected by nucleic acid hybridization using probes comprising sequences that are homologous to an inserted ANF gene. In the second approach, the recombinant vector/host system can be identified and selected based upon the presence or absence of certain "marker" gene functions (e.g., thymidine kinase activity, resistance to antibiotics, transformation phenotype, occlusion body formation in baculovirus, etc.) caused by the insertion of an ANF gene in the vector. For example, if the ANF gene is inserted within the marker gene sequence of the vector, recombinants containing the AMF insert can be identified by the absence of the marker gene function. In the third approach, recombinant expression vectors can be identified by assaying the ANF product expressed by the recombinant. Such assays can be based, for example, on the physical or functional properties of the ANF protein in in vitro assay systems, e.g., binding with anti-ANF antibody or the ANF receptor.

Once a particular recombinant DNA molecule is identified and isolated, several methods known in the art may be used to propagate it. Once a suitable host system and growth conditions are established, recombinant expression vectors can be propagated and prepared in quantity. As previously explained, the expression vectors which can be used include, but are not limited to, the following vectors or their derivatives: human or animal viruses such as vaccinia virus or adenovirus; insect viruses such as baculovirus; yeast vectors; bacteriophage vectors (e.g., lambda), and plasmid and cosmid DNA vectors, to name but a few.

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered ANF protein may be controlled. Furthermore, different host cells have characteristic and specific mechanisms for the translational and post-translational processing and modification (e.g., glycosylation, phosphorylation of proteins. Appropriate cell lines or host systems can be chosen to ensure the desired modification and processing of the foreign protein expressed. For example, expression in a bacterial system can be used to produce an unglycosylated core protein product. Expression in yeast will produce a glycosylated product. Expression in mammalian cells can be used to ensure "native" glycosylation of a heterologous protein. Furthermore, different vector/host expression systems may effect processing reactions to different extents.

In other specific embodiments, the ANF protein, fragment, analog, or derivative may be expressed as a fusion, or chimeric protein product (comprising the protein, fragment, analog, or derivative joined via a peptide bond to a heterologous protein sequence (of a different protein)). Such a chimeric product can be made by ligating the appropriate nucleic acid sequences encoding the desired amino acid sequences to each other by methods known in the art, in the proper coding frame, and expressing the chimeric product by methods commonly known in the art. Alternatively, such a chimeric product may be made by protein synthetic techniques, e.g., by use of a peptide synthesizer.

Both cDNA and genomic sequences can be cloned and expressed.

The ANF protein may also be isolated and purified by standard methods including chromatography (e.g., ion exchange, affinity, and sizing column chromatography), centrifugation, differential solubility, or by any other standard technique for the purification of proteins. The functional properties may be evaluated using any suitable assay (see Section 5.5). Alternatively, the protein can be synthesized by standard chemical methods known in the art (e.g., see Hunkapiller, M., et al., 1984, Nature 310:105–111).

In another alternate embodiment, native ANF proteins can be purified from natural sources, by standard methods such as those described above (e.g., immunoaffinity purification).

5.3. Method of Treatment

The present invention provides methods of treating and preventing ischemic diseases and disorders and cerebrovascular diseases and disorders (primarily stroke, preferably ischemic stroke) by administration of a therapeutic compound (termed herein "Therapeutic") of the invention. In one aspect of the invention, such "Therapeutics" include ANF mutant proteins and analogs, derivatives and fragments thereof (e.g., as described hereinabove) and nucleic acids encoding the mutant ANF proteins, analogs, derivatives, or fragments (e.g., as described hereinabove).

In one embodiment, the Therapeutic is a mutant ANF having one or more substitutions of amino acid residues relative to the wild type ANF protein, preferably, one or more amino acid substitutions in the amino acid residues selected from among amino-terminal residues 1–25, 1–20, 1–15, 1–10, 1–5 or 1–2 of ANF as depicted in FIGS. 2 or 5 (SEQ ID NOS: 1 and 4, respectively).

In a preferred embodiment, the Therapeutic is a mutant ANF having an amino acid substitution at amino acid position 1 of the rat ANF sequence provided in FIG. 2 (SEQ ID NO:1) or the corresponding position (i.e., as identified by aligning the amino acids having sequence identity between or among the rat ANF amino acid sequence and the amino acid sequence(s) of ANF proteins of other species) of the ANF protein of another species (preferably human ANF at amino acid position 1 as depicted in FIG. 5 (SEQ ID NO:4)), more preferably a mutant ANF where the amino acid at amino acid 1 of rat ANF as depicted in FIG. 2 (SEQ ID NO:1), or the at the corresponding amino acid position in a non-rat ANF protein (preferably amino acid position 1 of human ANF as depicted in FIG. 5 (SEQ ID NO:4)), is substituted by a residue that provides a substrate for kinase activity, e.g. a substitution with a residue from the group consisting of serine, threonine and tyrosine, preferably substitution with a serine residue. In another embodiment, an ANF mutant increases latency to stroke in stroke prone rats (e.g., rats having the stroke predisposing locus of chromosome 1) fed a high salt diet (for example,,but not limited to a diet of 17.5% protein, 3.7 mg/g Na$^+$, 6.3 mg/kg K$^+$, and 0.03 mg/g methionine and 1% NaCl drinking water) is administered to treat or prevent stroke.

The subject to which the Therapeutic is administered is preferably an animal, including but not limited to animals such as cows, pigs, horses, chickens, cats, dogs, etc., and is preferably a mammal. In a preferred embodiment, the subject is a human.

Generally, administration of products of a species origin or species reactivity (in the case of antibodies) that is the same species as that of the subject is preferred. Thus, in a preferred embodiment, a human mutant ANF protein, derivative, or analog, or nucleic acid, is therapeutically or prophylactically administered to a human patient.

The ANF mutants of the invention protective against stroke, particularly the ANF mutant having an amino acid substitution at position 1 of rat or human ANF as depicted in FIGS. 2 and 5, respectively (SEQ ID NOS:1 and 4, respectively), can be assayed by any of the methods described in Section 5.5 infra (for example, but not limited to, ANF receptor binding or signaling assays, e.g. as indicated by changes in cGMP levels, or detection of altered cGMP levels in plasma or urine, reduction in blood pressure, diuretic effect, etc., in vivo) to determine if the ANF mutant protective for stroke has higher or lower physiological activity than the wild type ANF. In the event it is determined that the mutant ANF proteins protective against stroke have a lower physiological activity than wild type ANF, then molecules that inhibit ANF activity (e.g. ANF antagonists and inhibitors), such as anti-ANF antibodies and ANF anti-sense nucleic acids, are also envisioned for use to treat or prevent ischemic disease, preferably ischemic stroke.

Accordingly, in a specific embodiment of the invention, ANF antagonists and inhibitors, including but not limited to anti-ANF antibodies (e.g. as described below) and ANF anti-sense nucleic acids (e.g. as described below) and ANF derivatives (e.g., that are competitive inhibitors of ANF) are administered to treat or prevent stroke or ischemic disease, preferably ischemic stroke.

Alternatively, in the event it is determined that the mutant ANF proteins protective against stroke have a higher physiological activity than wild type ANF, then ANF mutants having higher ANF activity and molecules that enhance ANF activity are also envisioned for use to treat or prevent stroke or ischemic disease, preferably ischemic stroke.

Accordingly, in a specific embodiment of the invention, ANF mutants having increased-ANF physiological activity relative to wild type ANF or molecules that enhance ANF activity are administered to treat or prevent stroke or ischemic disease, preferably ischemic stroke. In a more specific embodiment, ANF mutants that have a longer half life in vivo relative to wild type ANF are administered to treat or prevent ischemic disease, preferably ischemic stroke. The half-life of a protein is a measurement of protein stability and indicates the time necessary for a one-half reduction in the concentration of the protein. The half life of a mutant ANF can be determined by any method for measuring ANF levels in samples from a subject over-a period of time, for example but not limited to, immunoassays using anti-ANF antibodies to measure the mutant ANF levels in samples taken over a period of time after adminstration of the mutant ANF or detection of radiolabeled mutant ANF in samples taken from a subject after administration of the radiolabelled mutant ANF.

5.3.1. Ischemic Disease

In a preferred embodiment, Therapeutics of the invention are administered therapeutically, and preferably, prophylactically, to patients suffering from or in danger of suffering from stroke or an ischemic disease, preferably ischemic stroke, have previously suffered an cerebrovascular event, or exhibit one or more "risk factors" for stroke (i.e., a characteristic, behavior or disorder correlated with increased incidence of stroke) or one or more conditions associated with stroke. See generally, Albers and Cuttler, "Cerebrovascular Diseases", in Scientific American: Medicine, Volume 3 (Chapter 11:X), eds. Dale and Federman (Scientific American, Inc. 1994) and Barnett, "Cerebral Ischemia and Infarction" in Cecil Textbook of Medicine, eds. Wyngaarden and Smith, (W. B. Saunders Co. 1988) pp. 2162–2173.

A major indication of ischemic stroke predisposition is the incidence of Transient Ischemic Attacks (TIAs) which are brief and non-permanent episodes of neurologic dysfunction believed to result primarily from thromboembolism. Additionally, a variety of cranial blood vessel disorders can indicate a predisposition for stroke, e.g. atherosclerosis, particularly atherosclerosis associated with hypertension, diabetes mellitus, or coronary artery or peripheral vascular disease. Non-artherosclerotic angiopathies, particularly those associated with inflammation of the blood vessels, such as fibromuscular hyperplasia, dissecting aortic aneurism, Takayasu's disease, Mayamaya, allergic vasculitis, Congophilic angiopathy, vasculitis with homocystinuria, vasculopathy from drug abuse, vasculitis with Behgets disease, granulomatous angiitis, tuberculosis, temporal arteritis, collagen vascular disease or radiation injury. Trauma to the head and/or neck is also associated with a predisposition to stroke.

Patients suffering from cardiovascular disorders may also be predisposed to stroke. By way of example but not by way of limitation, acute myocardial infarction, heart block, hypertension, atrial fibrillation of any cause, bacterial and nonbacterial thrombotic endocarditis, atrial myxoma-neoplastic tissue, or implantation of a prosthetic heart valve can increase the likelihood that a patient will suffer an ischemic stroke.

Certain hematological diseases and disorders, particularly those associated with altered blood coagulation, more particularly with thromboses, also can increase the risk for stroke. Such hematological diseases include, but are not limited to, deficiencies of antithrombin III, protein C, or protein S, polycythemia vera, sickle cell anemia, disseminated intravascular coagulation, thrombotic thrombocytopenic purpura (TTP), paroxysmal nocturnal hemoglobinuria, hyperviscosity syndromes, macroglobulinemia, homocysteinura and lupus. Conditions or states such as shock, surgical anesthesia, pregnancy and post-partum, manifest and occult cancer, and stress due to trauma can also alter blood coagulation and increase the risk of stroke.

Other risk factors for stroke include, but are not limited to, ingestion of oral contraceptives, diabetes mellitus, migraine headaches, cigarette smoking and heavy alcohol consumption (although limited quantities may be protective), high or very low serum cholesterol levels, age, ingestion of substances such as amphetamines, cocaine or $\epsilon$-aminocaproic acid, and the presence of antiphospholipid antibodies.

In another embodiment, ischemic cardiovascular diseases and disorders are treated or prevented by administration of a Therapeutic of the invention. In a preferred embodiment, Therapeutics are administered to patients who exhibit one or more "risk factors" for ischemic cardiovascular disease, have a disease or disorder associated with predisposition to cardiovascular ischemic diseases or disorders, or have previously suffered from an ischemic cardiovascular event. See generally, Hutter, "Ischemic Heart Disease: Angina Pectoris" in Scientific American: Medicine (Chapter 1) Dale and Federman, eds. (Scientific American, Inc., 1995). Risk factors and disorders associated with increased risk of ischemic cardiovascular disease include atherosclerosis, angina, hypercholesterolemia, hypertension, obesity, smoking cigarettes, and other common risk factors for heart disease.

Therapeutics of the invention may be administered either alone or in combination with other therapies, e.g., therapeutics effective to treat or prevent ischemic cerebrovascular or cardiovascular disease. Therapeutics of the invention may also be administered with drugs which treat or ameliorate the effect of certain risk factors, for example but not by way of limitation, therapeutics that reduce cholesterol levels, treat obesity, diabetes mellitus, etc. In a preferred embodiment, a Therapeutic of the invention is administered with one or more anti-hypertensive drug such as, but not limited to, sympatholytics (such as propranolol, atenolol, nadolol, labetalol, prazosin, terazosin, doxazosin, clonidine, guanfacine, methyldopa, reserpine, etc.), angitension inhibitors (such as benazepril, captopril, enalapril, losartan), calcium channel blockers (such as diltiazem, felodipine, isradipine, nifedipine, verapamil), diuretics, e.g., thiazides (such as bendioflumethiazide, benzthiazide, hydrocholorothiazide, etc.), loop diuretics (such as bumetanide, ethacrynic acid, furosemide, and torsemide), potassium-sparing diuretics (such as amiloride, spironblactone and triametrene) and other diuretics, and vasodilators (such as hydralazine and minoxidil).

It is within the skill of those in the art to monitor and adjust the treatment or prophylactic regimen for treating or preventing ischemic cerebrovascular and/or ischemic cardiovascular disease while treating or preventing other potentially associated diseases or disorders, such as hypertension.

5.3.2. Gene Therapy

In a specific embodiment, nucleic acids comprising a sequence encoding a ANF mutant or derivative thereof or an ANF antisense nucleic acid, are administered by way of gene therapy. Gene therapy refers to therapy performed by the administration of a nucleic acid to a subject. In this embodiment of the invention, the nucleic acid produces its encoded protein or an antisense nucleic acid that mediates a therapeutic effect.

Any of the methods for gene therapy available in the art can be used according to the present invention. Exemplary methods are described below.

For general reviews of the methods of gene therapy, see Goldspiel et al., *Clinical Pharmacy* 12:488–505 (1993); Wu and Wu, *Biotherapy* 3:87–95 (1991); Tolstoshev, *Ann. Rev. Pharmacol. Toxicol.* 32:573–596(1993); Mulligan, *Science* 260:926–932 (1993); and Morgan and Anderson, *Ann. Rev. Biochem.* 62:191–217 (1993); May, *TIBTECH* 11:155–215 (1993)). Methods commonly known in the art of recombinant DNA technology which can be used are described in Ausubel et al. (eds.), *Current Protocols in Molecular Biology* (John Wiley & Sons, NY, 1993); and Kriegler, *Gene Transfer and Expression, A Laboratory Manual* (Stockton Press, NY, 1990).

In a preferred aspect, the Therapeutic comprises an ANF nucleic acid that is part of an expression vector that expresses an ANF protein or fragment or chimeric protein, preferably a mutant ANF protein or fragment or chimeric protein, or an ANF antisense nucleic acid thereof in a suitable host. In particular, such a nucleic acid has a promoter operably linked to the mutant ANF coding region or to a sequence encoding an ANF antisense nucleic acid, said promoter being inducible or constitutive, and, optionally, tissue-specific. In another particular embodiment, a nucleic acid molecule is used in which the mutant ANF coding sequences and any other desired sequences are flanked by regions that promote homologous recombination at a desired site in the genome, thus providing for intrachromosomal expression of the mutant ANF nucleic acid (Koller and Smithies, *Proc. Natl. Acad. Sci. USA* 86:8932–8935 (1989); Zijlstra et al., *Nature* 342:435–438 (1989)).

Delivery of the nucleic acid into a patient may be either direct, in which case the patient is directly exposed to the nucleic acid or nucleic acid-carrying vector, or indirect, in which case, cells are first transformed with the nucleic acid in vitro, then transplanted into the patient. These two approaches are known, respectively, as in vivo or ex vivo gene therapy.

In a specific embodiment, the nucleic acid is directly administered in vivo, where it is expressed to produce the encoded product. This can be accomplished by any of numerous methods known in the art, e.g., by constructing it as part of an appropriate nucleic acid expression vector and administering it so that it becomes intracellular, e.g., by infection using a defective or attenuated retroviral or other viral vector (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering it in linkage to a peptide which is known to enter the nucleus, by administering it in linkage to a ligand subject to receptor-mediated endocytosis (see e.g., Wu and Wu, *J. Biol. Chem.* 262:4429–4432 (1987)) (which can be used to target cell types specifically expressing the receptors), etc. In another embodiment, a nucleic acid-ligand complex can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, *Proc. Natl. Acad. Sci. USA* 86:8932–8935 (1989); Zijlstra et al., *Nature* 342:435–438 (1989)).

In a specific embodiment, a viral vector that contains the mutant ANF nucleic acid or codes for ANF antisense nucleic acid is used. For example, a retroviral vector can be used (see Miller et al., *Meth. Enzymol.* 217:581–599 (1993)). These retroviral vectors have been modified to delete retroviral sequences that are not necessary for packaging of the viral genome and integration into host cell DNA. The ANF nucleic acid to be used in gene therapy is cloned into the vector, which facilitates delivery of the gene into a patient. More detail about retroviral vectors can be found in Boesen et al., *Biotherapy* 6:291–302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644–651 (1994); Kiem et al., *Blood* 83:1467–1473 (1994); Salmons and Gunzberg, *Human Gene Therapy* 4:129–141 (1993); and Grossman and Wilson, *Curr. Opin. in Genetics and Devel.* 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Curr. Opin. in Genetics and Devel.* 3:499–503 (1993) present a review of adenovirus-based gene therapy. Bout et al., *Human Gene Therapy* 5:3–10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431–434 (1991); Rosenfeld et al., *Cell* 68:143–155 (1992); and Mastrangeli et al., *J. Clin. Invest.* 91:225–234 (1993).

Adeno-associated virus (AAV) has also been proposed for use in gene therapy (Walsh et al., *Proc. Soc. Exp. Biol. Med.* 204:289–300 (1993).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see e.g., Loeffler and Behr, *Meth. Enzymol.* 217:599–618 (1993); Cohen et al., *Meth. Enzymol.* 217:618–644 (1993); Cline, *Pharmac. Ther.* 29:69–92 (1985)) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. In a preferred embodiment, epithelial cells are injected, e.g., subcutaneously. In another embodiment, recombinant skin cells may be applied as a skin graft onto the patient. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, a mutant ANF nucleic acid or nucleic acid encoding an ANF antisense nucleic acid is introduced into the cells such that it is expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention. Such stem cells include but are not limited to hematopoietic stem cells (HSC), stem cells of epithelial tissues such as the skin and the lining of the gut, embryonic heart muscle cells, liver stem cells (PCT Publication WO 94/08598, dated Apr. 28, 1994), and neural stem cells (Stemple and Anderson, *Cell* 71:973–985 (1992)).

Epithelial stem cells (ESCs) or keratinocytes can be obtained from tissues such as the skin and the lining of the gut by known procedures (Rheinwald, *Meth. Cell Bio.* 21A:229 (1980)). In stratified epithelial tissue such as the skin, renewal occurs by mitosis of stem cells within the germinal layer, the layer closest to the basal lamina. Stem cells within the lining of the gut provide for a rapid renewal rate of this tissue. ESCs or keratinocytes obtained from the skin or lining of the gut of a patient or donor can be grown in tissue culture (Rheinwald, *Meth. Cell Bio.* 21A:229 (1980); Pittelkow and Scott, *Mayo Clinic Proc.* 61:771 (1986,)). If the ESCs are provided by a donor, a method for suppression of host versus graft reactivity (e.g., irradiation, drug or antibody administration to promote moderate immunosuppression) can also be used.

With respect to hematopoietic stem cells (HSC), any technique that provides for the isolation, propagation, and maintenance in vitro of HSC can be used in this embodiment of the invention. Techniques by which this may be accomplished include (a) the isolation and establishment of HSC cultures from bone marrow cells isolated from the future host, or a donor, or (b) the use of previously established long-term HSC cultures, which may be allogeneic or xenogeneic. Non-autologous HSC are used preferably in conjunction with a method of suppressing transplantation immune reactions of the future host/patient. In a particular embodiment of the present invention, human bone marrow cells can be obtained from the posterior iliac crest by needle aspiration (see, e.g., Kodo et al., *J. Clin. Invest.* 73:1377–1384 (1984)). In a preferred embodiment of the present invention, the HSCs can be made highly enriched or in substantially pure form. This enrichment can be accomplished before, during, or after long-term culturing, and can be done by any techniques known in the art. Long-term cultures of bone marrow cells can be established and maintained by using, for example, modified Dexter cell culture techniques (Dexter et al., *J. Cell Physiol.* 91:335 (1977)) or Witlock-Witte culture techniques (Witlock and Witte, *Proc. Natl. Acad. Sci. USA* 79:3608–3612 (1982)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Additional methods that can be adapted for use to deliver a nucleic acid encoding a ANF protein or functional derivative thereof are described in Section 5.6.

5.3.3. Antibodies

In one embodiment, as discussed hereinabove, antibodies that bind ANF proteins, ANF protein fragments or other derivatives, or analogs thereof are used to treat or prevent stroke or ischemic disease, preferably ischemic stroke. Anti-ANF antibodies can also be used in the diagnostic, prognostic and screening methods of the invention, e.g. as described in Section 5.4, infra. Such antibodies include, but are not limited to, polyclonal, monoclonal, chimeric, single chain, Fab fragments, and an Fab expression library. In a specific embodiment, antibodies to a human ANF protein are produced. In another specific embodiment, antibodies that reduce or inhibit ANF activity in vitro and/or in vivo, are provided.

Various procedures known in the art may be used for the production of polyclonal antibodies to an ANF protein or derivative or analog. In a particular embodiment, rabbit polyclonal antibodies to an epitope of an ANF protein (e.g. the protein of amino acid sequences SEQ ID NOS:1 and 4, or encoded by the nucleotide sequences of SEQ ID NOS:3 and 6, or a subsequence thereof), can be obtained. For the production of antibody, various host animals can be immunized by injection with the native ANF protein, or a synthetic version, or derivative (e.g., fragment) thereof, including but not limited to rabbits, mice, rats, etc. Various adjuvants may be used to increase the immunological response, depending on the host species, and including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum.

For preparation of monoclonal antibodies directed toward an ANF protein sequence or analog thereof, any technique which provides for the production of antibody molecules by continuous cell lines in culture may be used. For example, the hybridoma technique originally developed by Kohler and Milstein (*Nature* 256:495–497 (1975)), as well as the trioma technique, the human B-cell hybridoma technique (Kozbor et al., *Immunology Today* 4:72 (1983)), and the EBV-hybridoma technique to produce human monoclonal antibodies (Cole et al., in *Monoclonal Antibodies and Cancer Therapy*, Alan R. Liss, Inc., (1985) pp. 77–96). In an additional embodiment of the invention, monoclonal antibodies can be produced in germ-free animals utilizing recent technology (PCT/US90/02545). According to the invention, human antibodies may be used and can be obtained by using human hybridomas (Cote et al., *Proc. Natl. Acad. Sci. U.S.A.* 80:2026–2030 (1983)) or by transforming human B cells with EBV virus in vitro (Cole et al., in *Monoclonal Antibodies and Cancer Therapy*, Alan R. Liss, (1985) pp. 77–96). In fact, according to the invention, techniques developed for the production of "chimeric antibodies" (Morrison et al., *Proc. Natl. Acad. Sci. U.S.A.* 81:6851–6855 (1984); Neuberger et al., *Nature* 312:604–608 (1984); Takeda et al., *Nature* 314:452–454 (1985)) by splicing the genes from a mouse antibody molecule specific for ANF together with genes from a human antibody molecule of appropriate biological activity can be used; such antibodies are within the scope of this invention.

According to the invention, techniques described for the production of single chain antibodies (U.S. Pat. No. 4,946, 778) can be adapted to produce ANF-specific single chain antibodies. An additional embodiment of the invention utilizes the techniques described for the construction of Fab expression libraries (Huse et al., *Science* 246:1275–1281 (1989)) to allow rapid and easy identification of monoclonal Fab fragments with the desired specificity for ANF proteins, derivatives, or analogs.

Antibody fragments which contain the idiotype of the molecule can be generated by known techniques. For example, such fragments include but are not limited to: the F(ab')$_2$ fragment which can be produced by pepsin digestion of the antibody molecule; the Fab' fragments which can be generated by reducing the disulfide bridges of the F(ab')$_2$ fragment, the Fab fragments which can be generated by treating the antibody molecule with papain and a reducing agent, and Fv fragments.

In the production of antibodies, screening for the desired antibody can be accomplished by techniques known in the art, e.g. ELISA (enzyme-linked immunosorbent assay). For example, to select antibodies which recognize a specific portion of an ANF protein, one may assay generated hybridomas for a product which binds to an ANF fragment containing such portion. For selection of an antibody that can reduce or inhibit ANF activity, one can assay the antibody in any of the assays for ANF activity described in Section 5.7 infra.

5.3.4. Therapeutic Use of ANF Antisense Nucleuic Acids

In a specific embodiment, as described hereinabove, ANF function is reduced or inhibited by ANF antisense nucleic acids, to treat or prevent stroke or ischemic disease, preferably ischemic stroke. The present invention provides the therapeutic or prophylactic use of nucleic acids of at least six nucleotides that are antisense to a gene or cDNA encoding ANF or a portion thereof. An ANF "antisense" nucleic acid as used herein refers to a nucleic acid capable of hybridizing to a portion of an ANF RNA (preferably mRNA) by virtue of some sequence complementarily. The antisense nucleic acid may be complementary to a coding and/or noncoding region of an ANF mRNA. Because ANF is initially expressed as part the proANP hormone, "ANF mRNA" includes mRNA encoding the proANP hormone; and, thus, "ANF antisense nucleic acids" include nucleic acids that are capable of hybridizing to any portion of the proANP mRNA, including portions of the proANP mRNA coding for the other three hormones derived from proANP by proteolytic cleavage. Such antisense nucleic acids have utility as Therapeutics that reduce or inhibit ANF function, and can be used in the treatment or prevention of disorders as described supra.

The ANF antisense nucleic acids are of at least six nucleotides and are preferably oligonucleotides (ranging from 6 to about 150 nucleotides, or more preferably 6 to 50 nucleotides). In specific aspects, the oligonucleotide is at least 10 nucleotides, at least 15 nucleotides, at least 100 nucleotides, or at least 125 nucleotides. The oligonucleotides can be DNA or RNA or chimeric mixtures or derivatives or modified versions thereof, single-stranded or double-stranded. The oligonucleotide can be modified at the base moiety, sugar moiety, or phosphate backbone. The oligonucleotide may include other appending groups such as peptides, or agents facilitating transport across the cell membrane (see, e.g., Letsinger et al., *Proc. Natl. Acad. Sci. U.S.A.* 86:6553–6556 (1989); Lemaitre et al., *Proc. Natl. Acad. Sci. U.S.A.* 84:648–652 (1987); PCT Publication No. WO 88/09810, published Dec. 15, 1988) or blood-brain barrier (see, e.g., PCT Publication No. WO 89/10134, published Apr. 25, 1988), hybridization-triggered cleavage agents (see, e.g., Krol et al., *BioTechniques* 6:958–976 (1988)) or intercalating agents (see, e.g., Zon, *Pharm. Res.* 5:539–549 (1988)).

The ANF antisense nucleic acid is preferably an oligonucleotide, more preferably of single-stranded DNA. In a preferred aspect, the oligonucleotide comprises a sequence antisense to a portion of human ANF. The oligonucleotide may be modified at any position on its structure with substituents generally known in the art.

The ANF antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

In another embodiment, the oligonucleotide comprises at least one modified sugar moiety selected from the group including but not limited to arabinose, 2-fluoroarabinose, xylulose, and hexose.

In yet another embodiment, the oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the oligonucleotide is an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids Res.* 15:6625–6641 (1987)).

The oligonucleotide may be conjugated to another molecule, e.g., a peptide, hybridization triggered cross-linking agent, transport agent, hybridization-triggered cleavage agent, etc.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209 (1988)), methylphosphonate oligonucleotides can be prepared by use of controlled pore glass polymer supports (Sarin et al., *Proc. Natl. Acad. Sci. U.S.A.* 85:7448–7451 (1988)), etc.

In a specific embodiment, the ANF antisense oligonucleotide comprises catalytic RNA, or a ribozyme (see, e.g., PCT International Publication WO 90/11364, published Oct. 4, 1990; Sarver et al., *Science* 247:1222–1225 (1990)). In another embodiment, the oligonucleotide is a 2'-O-methylribonucleotide (Inoue et al., *Nucl. Acids Res.* 15:6131–6148 (1987)), or a chimeric RNA-DNA analogue (Inoue et al., *FEBS Lett.* 215:327–330 (1987)).

In an alternative embodiment, the ANF antisense nucleic acid of the invention is produced intracellularly by transcription from an exogenous sequence. For example, a vector can be introduced in vivo such that it is taken up by a cell, within which cell the vector or a portion thereof is transcribed, producing an antisense nucleic acid (RNA) of the invention. Such a vector would contain a sequence encoding the ANF antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the ANF antisense RNA can be by any promoter known in the art to act in mammalian, preferably human, cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc.

The antisense nucleic acids of the invention comprise a sequence complementary to at least a portion of an RNA transcript of an ANF gene, preferably a human ANF gene. However, absolute complementarily, although preferred, is not required. A sequence "complementary to at least a portion of an RNA," as referred to herein, means a sequence having sufficient complementarily to be able to hybridize with the RNA, forming a stable duplex; in the case of double-stranded ANF antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with a an ANF RNA it may contain and still form a stable duplex (or triplex, as the case may be). One skilled in the art can ascertain a tolerable degree of mismatch by use of standard procedures to determine the melting point of the hybridized complex.

The invention further provides pharmaceutical compositions comprising an effective amount of the ANF antisense nucleic acids of the invention in a pharmaceutically acceptable carrier, as described infra. In a specific embodiment, pharmaceutical compositions comprising ANF antisense nucleic acids are administered via liposomes, microparticles, or microcapsules. In various embodiments of the invention, it may be useful to use such compositions to achieve sustained release of the ANF antisense nucleic acids.

The amount of ANF antisense nucleic acid which will be effective in the treatment or prevention of ischemic disease will depend on the nature of the disease, and can be determined by standard clinical techniques. Where possible, it is desirable to determine the antisense cytotoxicity in cells in vitro, and then in useful animal model systems prior to testing and use in humans.

Additional methods that can be adapted for use to deliver a ANF antisense nucleic acid are described in Section 5.6 infra.

5.4. Methods of Diagnosis, Prognosis and Screening

The present invention also relates to methods of diagnosis, prognosis and screening for stroke or ischemic disease, preferably ischemic stroke, including but not limited to in those subjects having ischemic disease or stroke, having previously suffered an cerebrovascular event or exhibit one or more "risk factors" for stroke or one or more conditions associated with stroke. In a preferred aspect, the invention relates to methods for screening for an allele protective against stroke.

In one embodiment, anti-ANF-antibodies are used to detect and quantitate mutant ANF levels in one or more tissues (e.g., blood) of a subject in immunoassays.

In particular, such an immunoassay is carried out by a method comprising contacting a sample derived from a patient with an anti-ANF antibody under conditions such that immunospecific binding can occur, and detecting or measuring the amount of any immunospecific binding by the antibody. The particular amino acid deletion, insertion or substitution in the mutant ANF can change the epitope recognized by a specific anti-(wild type) ANF antibody such that antibody binds the mutant ANF to a lesser extent or not at all. Additionally, antibodies can be raised (e.g. as described in Section 5.3.3 supra) against the mutant ANF protein, or portion thereof, that bind specifically to the particular mutant ANF, but not the wild type ANF (as determined by the in vitro immunoassays described below). These specific anti-mutant ANF antibodies can be used to detect the presence of ANF mutants by measuring the immunospecific binding by the anti-mutant ANF antibodies and, optionally, lack of immunospecific binding by the anti-(wild type) ANF antibodies. Additionally, ANF proteins having deletion or insertion mutations can be detected by an increase or decrease in protein size by, for example, but not limited to, western blot analysis using an anti-ANF antibody that recognizes the mutant and wild-type ANF.

The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few.

In a specific embodiment, methods of diagnosis, prognosis and screening by detecting mutant ANF alleles in genomic DNA or mRNA (i.e. genetic screening) are provided. Preferably, mutant alleles known to be protective for stroke are detected in genomic DNA or cDNA derived from mRNA from a subject. In a preferred embodiment, methods for detecting an amino acid substitution at the position corresponding to amino acid 1 of the rat or human ANF amino acid sequence as depicted in FIGS. 2 or 5, respectively (SEQ ID NOS:1 or 4, respectively) are provided for assessing an allele protective for stroke. The mutant ANF alleles can be detected by any method known in the art for detecting mutations in genomic DNA. By way of example but not by way of limitation, DNA hybridization methods (e.g. Southern Blotting), RFLP mapping, PCR based methods, etc. can be used with nucleic acid probes complementary to the mutation and to the corresponding position in the wild type sequence.

In a preferred embodiment, allele-specific PCR (ASP) can be used to detect mutant ANF alleles. In ASP, a target DNA is preferentially amplified if it is completely complementary to the 3' end of a PCR amplification primer. The 3' end of the primer should terminate at or within one or two bases of a known mutation site in the ANF gene (target DNA) to which it has a complementary sequence. Under the appropriate reaction conditions, the target DNA is not amplified if there is a base mismatch (e.g., a nucleotide substitution caused by a mutation) or a small deletion or insertion, at the 3' end of the primer (Okayama et al. *J. Lab. Clin. Med.* 114:105–113 (1989); Sommer et al., *BioTechniques* 12:82–87 (1992). Thus, ASP can be used to detect the presence or absence of at least a single mismatch between the primer sequence that is complementary to the preselected target sequence and a nucleic acid in the sample; amplification indicates the absence of such a single mismatch. Preferred ASP primers for detecting a mutation in the position corresponding to amino acid 1 of rat ANF include 5'-AGATGGAGGTGCTCTCGGGCGCA-3' (SEQ ID NO:11). The wild type locus can be detected using a primer 5'-AGATGGAGGTGCTCTCGGGCGCG-3' (SEQ ID NO:12). Preferred ASP primers for detecting a mutation in the position corresponding to amino acid 1 of human ANF include 5'-AGAGATGGAGGTGCCCTCGGGCGGA-3' (SEQ ID NO:13). The wild type locus can be detected using a primer 5'-AGAGATGGAGGTGCCCTCGGGCGGG-3' (SEQ ID NO:14).

Additionally, where the mutant is a deletion or insertion mutation, mutant ANF alleles can be detected by assaying for an increase or decrease in the length of the ANF nucleotide sequence or portion thereof. The increase or decrease in length can be detected by any method known in the art for measuring the length of nucleic acids, for example, but not limited to, by amplification of a specific fragment of the ANF sequence from the subject to be diagnosed or screened and from a standard or control sample and comparison of the length of the fragments by any size fractionation method, such as but not limited to, denaturing polyacrylamide gel electrophoresis.

Kits for diagnostic or screening use are also provided that comprise in one or more containers an anti-ANF antibody or anti-ANF mutant antibody, and, optionally, a labeled binding partner to the antibody. Alternatively, the anti-ANF antibody or anti-ANF mutant antibody can be labeled (with a detectable marker, e.g., a chemiluminescent, enzymatic, fluorescent, or radioactive moiety). A kit is also provided that comprises in one or more containers a nucleic acid probe capable of hybridizing to ANF RNA or, preferably, capable of specifically hybridizing to mutant ANF. In a specific embodiment, a kit can comprise in one or more containers a pair of primers (e.g., each in the size range of 6–30 nucleotides) that are capable of priming amplification [e.g., by polymerase chain reaction (see e.g., Innis et al., PCR Protocols (Academic Press, Inc., San Diego, Calif. (1990)), ligase chain reaction (see EP 320,308) use of Qβ replicase, cyclic probe reaction, or other methods known in the art] under appropriate reaction conditions of at least a portion of a ANF nucleic acid. A kit can optionally further comprise in a container a predetermined amount of a purified ANF protein or nucleic acid, e.g., for use as a standard or control.

5.5. Assays for ANF Mutants and Modulators of ANF

A variety of methods are available in the art for assaying the activity of ANF mutants, derivatives, analogs, fragments and homologs of ANF mutants, and nucleic acids encoding the ANF mutants and derivatives, analogs and fragments thereof. Methods are also available for the screening of putative ANF modulators (e.g. ANF agonists, antagonists and inhibitors). Such modulators of ANF activity include, but are not limited to, ANF antisense nucleic acids, anti-ANF antibodies, and competitive inhibitors of ANF for binding to the ANF receptor.

In vitro methods for assaying ANF mutant protein, and derivatives, fragments, homologs and analogs thereof, the nucleic acids encoding these ANF mutants, and putative modulators of ANF (e.g. agonists, antagonists or inhibitors of ANF activity) include, but are not limited to, ANF receptor binding assays, such as those described by Vesely et al. (*Renal Phys. & Biochem.* 15:23–32 (1992)), Iwashina et al. (*J. Biochem.* 115 563–567 (1994)), de Leon et al. (*J. Hypertens.* 12:539–548 (1994)), He et al. (*Bioconjugate Chem.* 6:541–548 (1995)), and Chang et al. (*Curr. Eye Res.* 15:137–143 (1996)); measurement of changes in cGMP concentrations in cells having ANF receptors, e.g., by methods described by Schulz et al. (*Cell* 58:1155–1162 (1989)) and Wedel et al. (*Proc. Natl. Acad. Sci. U.S.A.* 21:459–462 (1997)); and changes in intracellular $Ca^{2+}$ resulting from ANF receptor signalling in response to ANF binding, e.g. as described by Nascimento-Gomes et al. (*Brazil. J. of Med. & Biol. Res.* 28:609–613 (1995)). However, any measurement of ANF receptor activity elicited by ANF binding can be used to assay ANF activity in vitro.

The activity of the ANF mutants, derivatives, fragments, analogs and homologs of ANF mutants, the nucleic acids encoding these ANF mutants, and derivatives, fragments, analogs and homologs of ANF mutants, and putative modulators of ANF activity can also be tested in vivo. For example, infusion of ANF in humans causes significant increases in cGMP levels in plasma and urine (Vesely et al., *Am. J. Med. Sci.* 310:143–149 (1995); Vesely et al., *Metabolism: Clin. & Exp.* 45:315–319 (1996)). Administration of ANF to humans also elicits significant diuresis and reduction in blood pressure (Vesely et al., *Life Sciences* 59:243–254 (1996)); similar effects have been observed in rats (Garcia et al., *Hypertension* 13:567–574 (1989)). Accordingly, the mutant ANF proteins and nucleic acids, and derivatives, analogs, fragments, and homologs thereof, and putative ANF modulators can be assayed by administration of the test compound to a test animal, preferably a non-human test animal such as a rat or mouse, and then measurement of the one or more of the physiological parameters described above, e.g. cGMP levels in urine and/or plasma, diuretic effect, decrease in blood pressure, etc.

In a preferred embodiment, rats derived from crosses with SHRSP animals are used to assay for ANF activity or ANF modulator activity. For example, rats that have the stroke-predisposing locus on chromosome 1 and lack the stroke-protective locus on chromosome 5 that maps to the ANF gene (and optionally the other stroke-protective locus on chromosome 4) can be used to screen for ANF mutants and putative ANF antagonists. In particular, nucleic acids containing the nucleotide sequence encoding an ANF mutant can be introduced into the rats having the chromosome 1 stroke predisposing locus but not the stroke protective loci. ANF mutants useful for treatment and prevention of stroke would increase stroke latency when either administered or expressed transgenically in the stroke prone rats lacking the two protective loci and fed a high salt diet.

In one embodiment, a putative modulator of ANF activity or of latency or predisposition to stroke is screened by (a) administering a putative modulator of ANF activity to an animal prone to stroke, and (b) measuring one or more physiological parameters associated with ANF activity, in which a change in said one or more parameters relative to an animal not administered the putative modulator indicates that the putative modulator modulates ANF activity or latency or predisposition to stroke. In a specific embodiment, the animal prone to stroke is fed a high salt diet. In a preferred embodiment, the physiological parameter is stroke latency. Additionally, ANF modulators can be screened using a recombinant test animal which expresses an ANF transgene or expresses ANF under the control of a promoter that is not the native ANF gene promoter at an increased level relative to a wild type test animal.

Another embodiment provides a method for screening an ANF mutant for a change in ANF activity comprising (a) administering the ANF mutant to a test animal prone to stroke; and (b) measuring stroke latency in the test animal in which stroke latency is indicative of ANF activity. In a specific embodiment, a recombinant test animal which expresses an ANF transgene or expresses ANF under the control of a promoter that is not the native ANF gene promoter at an increased level relative to a wild type test animal is used to screen ANF mutants for a change in ANF activity.

In yet another embodiment, a method for screening for a modulator of ANF activity or of latency or predisposition to stroke is provided which comprises measuring stroke latency in a stroke prone animal that recombinantly expresses a putative modulator of ANF activity, in which a change in stroke latency relative to an analogous stroke prone animal that does not recombinantly express the putative modulator indicates that the putative modulator modulates ANF activity or latency or predisposition to stroke.

In another embodiment, a method is provided for screening an ANF mutant for an effect on latency or predisposition to stroke comprising measuring stroke latency in a stroke prone animal that recombinantly expresses an ANF mutant, in which a change in stroke latency relative to an analogous stroke prone animal that does not recombinantly express the ANF mutant indicates that the ANF mutant has an effect on latency or predisposition to stroke. In a preferred embodiment, an ANF mutant is screened for an increase in stroke latency or a decrease in predisposition to stroke.

5.6. Pharmaceutical Compositions

The invention provides methods of treatment and prophylaxis by administering to a subject of an effective amount of a Therapeutic of the invention. In a preferred aspect, the Therapeutic is substantially purified. The subject is preferably an animal, including but not limited to animals such as cows, pigs, horses, chickens, cats, dogs, etc., and is preferably a mammal, and most preferably human. In a specific embodiment, a non-human mammal is the subject.

Formulations and methods of administration that can be employed when the Therapeutic comprises a nucleic acid are described in Sections 5.3.2 and 5.3.4 above; additional appropriate formulations and routes of administration can be selected from among those described hereinbelow.

Various delivery systems are known and can be used to administer a Therapeutic of the invention, e.g., encapsulation in liposomes, microparticles, microcapsules, recombinant cells capable of expressing the Therapeutic, receptor-mediated endocytosis (see, e.g., Wu and Wu, *J. Biol. Chem.* 262:4429–4432 (1987)), construction of a Therapeutic nucleic acid as part of a retroviral or other vector, etc. Methods of introduction include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers.

In another embodiment, the Therapeutic can be delivered in a vesicle, in particular a liposome (see Langer, *Science* 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the Therapeutic can be delivered in a controlled release system. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 35 115–138 (1984)).

Other controlled release systems are discussed in the review by Langer (*Science* 249:1527–1533 (1990)).

In a specific embodiment where the Therapeutic is a nucleic acid encoding a protein Therapeutic, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., *Proc. Natl. Acad. Sci. USA* 88:1864–1868 (1991)), etc. Alternatively, a nucleic acid Therapeutic can be introduced intracellularly and incorporated within host cell DNA for expression, by homologous recombination.

The present invention also provides pharmaceutical compositions. Such compositions comprise a therapeutically effective amount of a Therapeutic, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use-in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the Therapeutic, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The Therapeutics of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the Therapeutic of the invention which will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20–500 micrograms of active compound per kilogram body weight. Suitable dosage ranges for intranasal administration are generally about 0.01 pg/kg body weight to 1 mg/kg body weight. Effective doses may be extrapolated from dose-response curves derived from in vitro or animal model test systems.

Suppositories generally contain active ingredient in the range of 0.5% to 10% by weight; oral formulations preferably contain 10% to 95% active ingredient.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

5.7. Animal Models

The invention also provides animal models.

In one embodiment, animal models for stroke or ischemic disease, specifically ischemic stroke (e.g., as described in Section 5.8) are provided. In one embodiment, SHRSP animals are bred with normal or non-stroking rats not having a mutant ANF allele. Rats can be selected that have the chromosome 1 locus for stoke predisposition but do not have the chromosome 5 locus (i.e. have a wild type ANF locus) or, optionally the chromosome 4 locus, demonstrated to be protective for stroke in the SHRSP strain. Such animals can be used to test for mutant ANF proteins with reduced activity or for ANF antagonists as described in Section 5.7 supra.

Additionally, transgenic animals can be generated that overexpress or misexpress the ANF gene, e.g. by introducing the ANF gene under the control of a heterologous promoter or a promoter that causes the expression of ANF in tissues not normally expressing ANF. Additionally, "knockout" mice can be initially produced by promoting homologous recombination between a ANF gene in its chromosome and an exogenous ANF gene that has been rendered biologically inactiye (preferably by insertion of a heterologous sequence, e.g., an antibiotic resistance gene) or by non-homologous recombination. In a preferred aspect, introduction of heterologous DNA is carried out by transforming embryo-derived stem (ES) cells with a vector containing the insertionally inactivated ANF gene or ANF gene under the control of a heterologous promoter, followed by injecting the ES cells into a blastocyst, and implanting the blastocyst into a foster mother. The resulting mice are chimeric animals ("knockout animal" or "transgenic animal") in which an ANF gene has been inactivated or overexpressed or misexpressed (see Capecchi, *Science* 244:1288–1292 (1989)). The chimeric animal can be bred to produce additional knockout or transgenic animals. Such animals can be mice, hamsters, sheep, pigs, cattle, etc., and are preferably non-human mammals. Transgenic and knockout animals can also be made in *D. melanogaster, C. elegans,* etc. by methods that are commonly known in the art.

One embodiment of the invention provides a recombinant non-human animal containing a mutant ANF gene under the control of a promoter that is not the native ANF gene promoter, in which the mutant ANF gene encodes a mutant ANF that increases latency to stroke. Another embodiment of the invention provides a recombinant non-human animal that is the product of a process comprising introducing a nucleic acid into the non-human animal, or an ancestor thereof, said nucleic acid comprising a mutant ANF gene sequence.

6. EXAMPLE

Heart tissue from SHRSP, SHR and WKY rats was analyzed by QEA™ to identify and characterize genes that are differentially expressed in the SHRSP rats as compared to the SHR and WKY rats.

6.1. Materials and Methods

SHRSP, SHR, and WKY rats were maintained on normal rat chow and water ad libitum. Thirteen week old rats were sacrificed and the hearts removed. The hearts were quick frozen in liquid nitrogen immediately after dissection, and stored at −70° C. until processing for QEA™.

Total cellular RNA was extracted from 5 mg of heart tissue by first grinding the tissue into a fine powder on liquid nitrogen. The tissue powder was transferred to a tube containing 500 μl Triazol reagent (see Chomszynski et al. 1987, *Annal. Biochem.* 162 156–159 and Chomszynski et al., 1993, *Biotechniques* 15:532–532,536–537; reagent obtained from Life Technologies, Gaithersburg, Md.) and was dispersed in the Triazol using a Polytron homogenizer from Brinkman Instruments (Westbury, N.Y.). The cellular RNA fraction was extracted with 50 μl BCP (1-bromo-3-chloropropane) (Molecular Research, Cincinnati, Ohio). The extraction mixture was centrifuged for 15 minutes at 4° C. at 12,000× G, and the aqueous phase was removed to a fresh tube. The RNA was then precipitated with 0.5 volumes isopropanol per original amount of Triazol reagent used, and the sample centrifuged at room temperature for 10 minutes at 12,000× G. The supernatant was discarded, the pellet washed with 70% ethanol and then centrifuged at room temperature for 5 minutes at 12,000× G. Finally the 70% ethanol was removed and the centrifuge tube was let stand to dry in an inverted position. The resulting RNA pellet was resuspended in 100 μl water (1 μl per mg of original tissue weight) and heated to 55° C. until completely dissolved.

The RNA samples were then treated with DNAse to remove DNA. 28 μl of 5× reverse transcriptase buffer (Life Technologies, Gaithersburg, Md.), 10 μl 0.1 M DTT, and 5 units RNAguard per 100 mg starting tissue (Pharmacia Biotech, Uppsala, Sweden) and 1 unit RNase-free DNase I (Pharmacia Biotech) per 100 mg starting tissue were added to the resuspended RNA samples. The reaction mixture was incubated at 37° C. for 20 minutes. The total RNA concentration was quantified by measuring $OD_{260}$ of a 100 fold dilution and the samples stored at −20° C.

Poly-adenylated mRNA was isolated from the total RNA preparations using magnetic bead mediated oligo-dT detection with the Dynabeads MRNA Direct Kit from Dynal (Oslo, Norway) as directed by the manufacturer. The poly-adenylated RNA was harvested in a small volume of water, quantified by $OD_{260}$ measurement, and stored at −20° C.

cDNA was synthesized from the poly-adenylated RNA as follows:

The poly A+ RNA was mixed with 50 ng random hexamers (50 ng/μl) in 10 μl of water. The mixture was heated to 70° C. for 10 minutes, quick chilled in ice-water slurry, and kept on ice for 1–2 min. The condensate was collected by centrifugation in a microfuge for 10 seconds.

The first strand synthesis was carried out by adding a reaction mixture of 4 μl 5× first strand buffer (from the BRL kit), 2 μl 100 mM DTT, 1 μl 10 mM dNTP mix, and 2 μl water to the primer-annealed RNA. The reaction mixtures were incubated at 37° C. for 2 mins, 1 μl of Superscript II (BRL) (following manufacturer's recommendations) was added, and the reactions were then incubated at 37° C. for 1 hr.

To synthesize the second cDNA strand, the samples were placed on ice, 30 μl of 5× Second strand buffer, 90 μl of cold water, 3 μl of 10 mM DNTP, 1 μL (10 units) of *E. coli* DNA ligase (BRL), 4 μl (40 units) of *E. coli* DNA polymerase (BRL), and 1 μl (3.5 units) of *E. coli* RNaseH (BRL) were added to the tubes, and the reactions were incubated for 2 hours at 16° C. The resulting cDNA was then incubated with 2 μl of T4 DNA polymerase (5 units) at 16° C. for 5 min.

The resulting cDNA was dephosphorylated with Arctic Shrimp Alkaline Phosphatase ("SAP"; obtained from USB); 20 μl 10× SAP buffer, 25 μl of water, and 5 μl (5 units) of SAP were added to the reaction mixtures and incubated at 37° C. for 30 min.

The cDNA was extracted with phenol-chloroform, chloroform-isoamyl alcohol, precipitated from the aqueous phase by addition of Na-acetate to 0.3 M, 20 μg glycogen, and 2 vol of ethanol, incubation at −20° C. for 10 min., and collected by centrifugation at 14,000 g for 10 min. The supernatant was removed and the pellet washed with 75% ethanol, resuspended in TE, and the cDNA quantitated.

For subsequent QEA™ processing, 75 ng cDNA was transferred to a separate tube, resuspended in TE to a concentration 600 ng/ml, and stored at −20° C. QEA™ analysis (see PCT Publication WO 97/15690 dated May 1, 1997) was performed with BsrFI and BglII restriction enzymes. Adapter molecules for the QEA™ analysis were prepared from linker and primer oligonucleotides. For the "sticky ends" generated by the BsrFI restriction enzyme, the linker oligonucleotide 5'-GGCCCGAAGTACA-3'(SEQ ID NO:15) and the primer oligonucleotide 5'-GGCCCGAAGTAC-3' (SEQ ID NO:16) were used. For the BglII reaction "sticky ends", the linker oligonucleotide 5'-GGCCCAGCCACT-3' (SEQ ID NO:17) and the primer oligonucleotide 5'-GGCCCAGCCAC-3' (SEQ ID NO:18) were used. One set of primers were labeled with FAM fluorescent label and one set were labeled with a biotin moiety. The adapters were prepared by mixing the linker and primer oligonucleotides together in water at a concentration ratio of 1:20 (linker to primer) with the primer at a total concentration of 50 pm per μl. The mixture was incubated at 50° C. for 10 minutes and then allowed to cool slowly to room temperature to anneal the linkers and primers. The adapters were stored at −20° C.

The QEA™ reactions were performed using an automated QEA™ procedure. Reactions were preformed in a standard 96 well thermal cycler format using a Beckman Biomek 2000 robot (Beckman, Sunnyvale, Calif.). The 3 cDNA samples were analyzed in triplicate with BsrFI and BglII restriction enzymes. All steps were performed by the robot, including solution mixing, from user provided stock reagents, and temperature profile control.

The RE/ligase reaction contained the following components per reaction:

1. 1 U each BsrFI and BglII (New England Biolabs, Beverly, Mass.)
2. 1 μl of each annealed adapter prepared as above (10 pm)
3. 0.1 μl T4 DNA ligase [1 U/μl] (Life Technologies (Gaithersburg, Md.)
4. 1 μl ATP (Life Technologies, Gaithersburg, Md.)

5. 5 ng of the prepared cDNA
6. 1.5 µl 10× NEB 2 buffer from New England Biolabs (Beverly, Mass.)
7. 0.5 µl of 50 mM MgCl$_2$
8. Water to bring total volume to 10 µl and transfer to thermal cycler.

The robot performed the RE/ligation reaction in a PTC-100 Thermal Cycler equipped with a mechanized lid from MJ Research (Watertown, Mass.) with the following temperature profile: 15 minutes at 37° C., ramp down 21° C. in 5 minutes, 16° C. for 30 minutes, 37° C. for 10 minutes, and 65° C. for 10 minutes.

The PCR reaction mix contained the following components per reaction:

1. 10 µl 5× E-Mg (300 mM Tris-HCl pH 9.0, 75 mM (NH$_4$)$_2$SO$_4$)
2. 100 pm of BsrFI and BglII primers (SEQ ID NOS:16 and 18, respectively) (one set labeled with FAM; the other set labeled with biotin).
3. 1 µl 10 mM dNTP mix (Life Technologies, Gaithersburg, Md.)
4. 2.5 U of 50:1 Taq polymerase (Life Technologies, Gaithersburg, Md.): Pfu polymerase (Stratagene, La Jolla, Calif.)
5. Water to being volume to 35 µl per PCR reaction The PCR mix was heated to 72° C. and 35 µl was transferred to each digestion/ligation reaction. The PTC-100 Thermal Cycler then performed the PCR reaction with a thermal profile of 72° C. for 10 minutes, 15 cycles of 95° C. for 30 seconds and 68° C. for 1 minute, and then 72° C. for 10 minutes, and finally holding the reactions at 4° C.

Before further analysis, the QEA products were subjected to a post-PCR clean up protocol as follows:

1. Streptavidin magnetic beads (Catalog No. MSTR0510 of CPG, Lincoln Park, N.J.) were prepared (3 µl of beads for every 5 µl of QEA™ reaction product) by pre-washing beads in 10 µl binding buffer (5 M NaCl, 10 mM Tris, pH 8.0, 1 mM EDTA) per 5 µl original volume of QEA™ reaction product.
2. 10 µl of washed beads were dispensed in a 96 well FALCON™ TC plate for every QEA™ sample processed.
3. QEA™ products were added to the beads, mixed well and incubated for 30 minutes at 50° C.
4. The sample volume was made 100 µl with binding buffer, the plate placed on a 96 well magnetic particle concentrator, and the beads allowed to migrate for 5 minutes.
5. The liquid was then removed, and 200 µl washing buffer (10 mM Tris, pH 7.4, 10 mM EDTA) added per well.
6. Washing step 5 was repeated.

For analysis, the beads were resuspended in 5 µl loading buffer (80% deionized formamide, 20% 25 mM EDTA, pH 8.0, 50 mg/ml Blue dextran) per 5 µl of beads, and the supernatant WAs then analyzed by electrophoresis on an ABI 377 (Applied Biosystems, Inc.) automated sequencer under denaturing conditions using the Gene Scan software (ABI) for analysis. The GeneScan 500 ROX ladder was diluted 1:10 in loading buffer and analyzed as a size control.

"Oligonucleotide poisoning" was performed to confirm that the differentially expressed fragment was derived from ANF. Essentially, an unlabeled oligonucleotide having a nucleotide sequence able to hybridize to the ANF sequence (and prevent amplification with the labeled primers) was included in a PCR reaction using the QEA™ reaction products as substrate. The specific "poisoning" primer has the sequence 5'-AAGATGCCGGTAGAAG-3' (SEQ ID NO:19).

Specifically, for the oligonucleotide poisoning, each reaction mixture contained 1 µl of a 1:100 dilution of the QEA™ reaction products, 5 µl TB 2.0 (500 mM Tris-HCl pH 9.15, 160 mM (NH$_4$)$_2$SO$_4$, 20 mM MgCl$_2$), 2 µl 10 mM equimolar mixture of all four dNTPs, 0.2 µl each BsrFI and BglII primers (100 pm/ml), 2 µl ANF poisoning primer (1000 pm/ml), 1 µl 5 M betaine, 1 µl NEB 2 buffer (10 mM Tris-HCl, 10 mM MgCl$_2$, 50 mM NaCl, 1 mM DTT (pH 7.9 at 25° C.), 0.25 µl 25 U/ml of a 16:1 mixture of Klentaq:pfu, and 38 µl water.

The following PCR temperature protocol was performed in a thermal cycler for 13 cycles:

96° C. for 30 seconds;
57° C. for 1 minute;
72° C. for 2 minutes.

The amplified products were held at 4° C. and then analyzed as described above on the automatic sequencer.

6.2. Results

Quantitative Expression Analysis (QEA™) was used to compare the gene expression profiles of hearts from WKY, SHR and SHRSP rats fed a normal diet. The QEA™ method enables comparison of the level of expression of all transcribed sequences among the samples with a sensitivity of 1 part in 125,000. A total of 12,000 gene fragments, generated from approximately 6000 genes, were compared between hearts samples of each rat strain in triplicate. The comparison between the WKY and SHR rat yielded 68 different fragments (0.6%), the SHR and SHRSP comparison yielded 29 differences (0.02%), and the WKY and SHRSP comparison yielded 97 differences (0.8%).

Figure 1C:
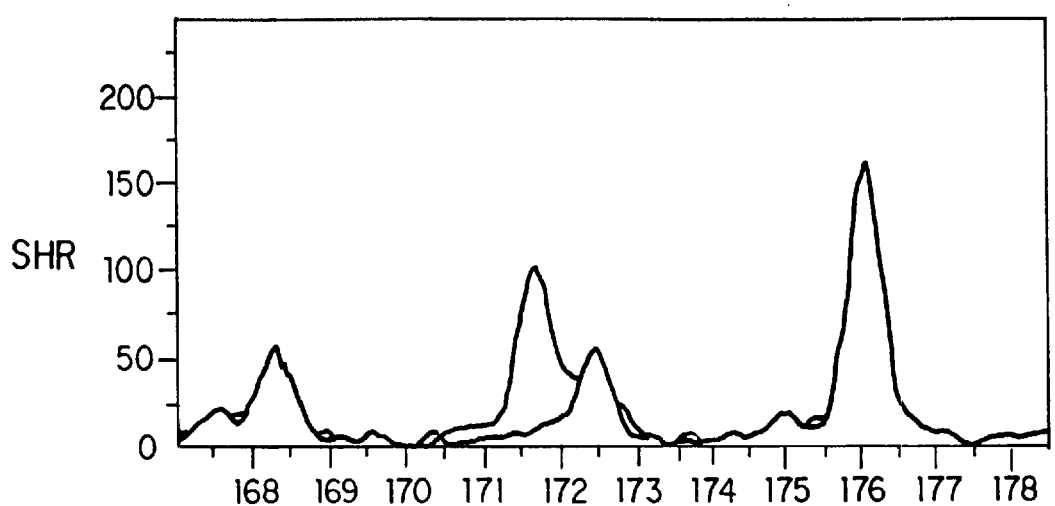
Figure 1D:
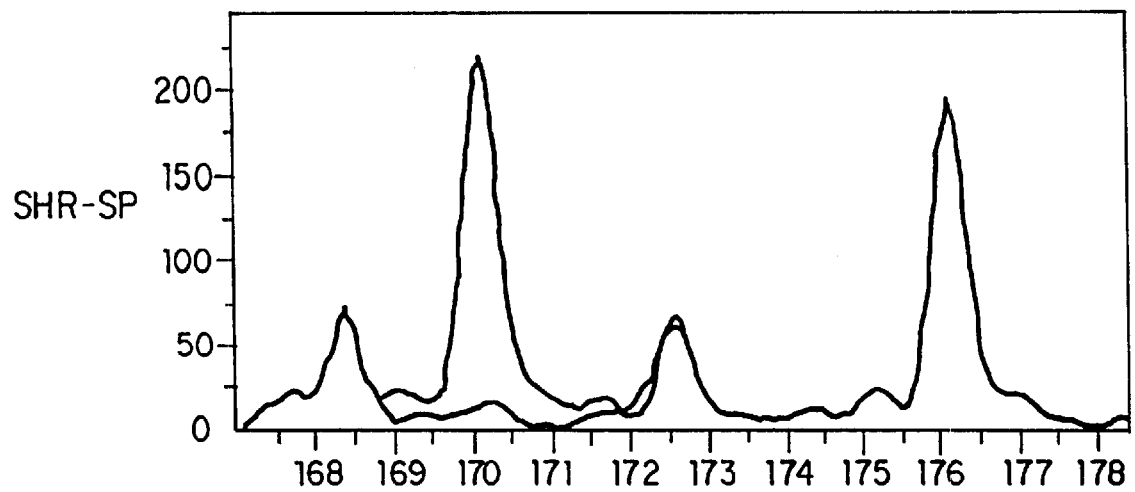
Figure 1E:
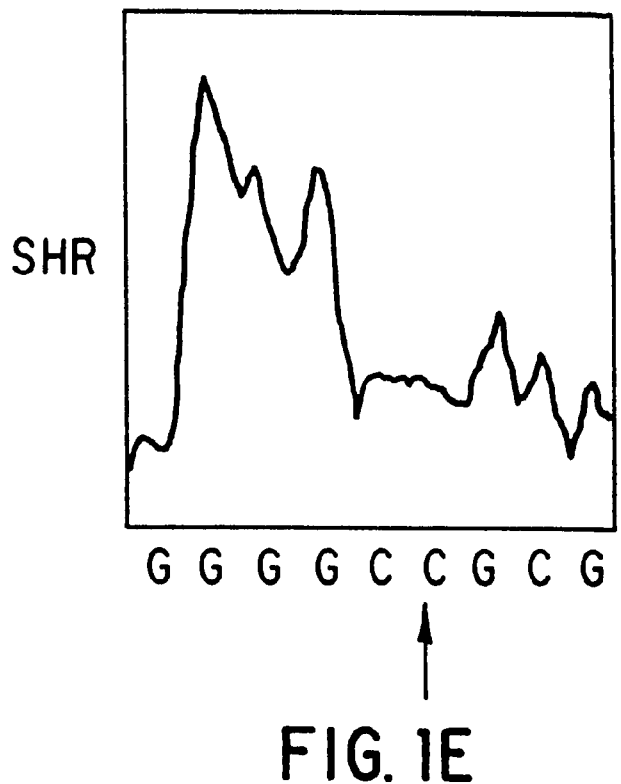
Figure 1F:
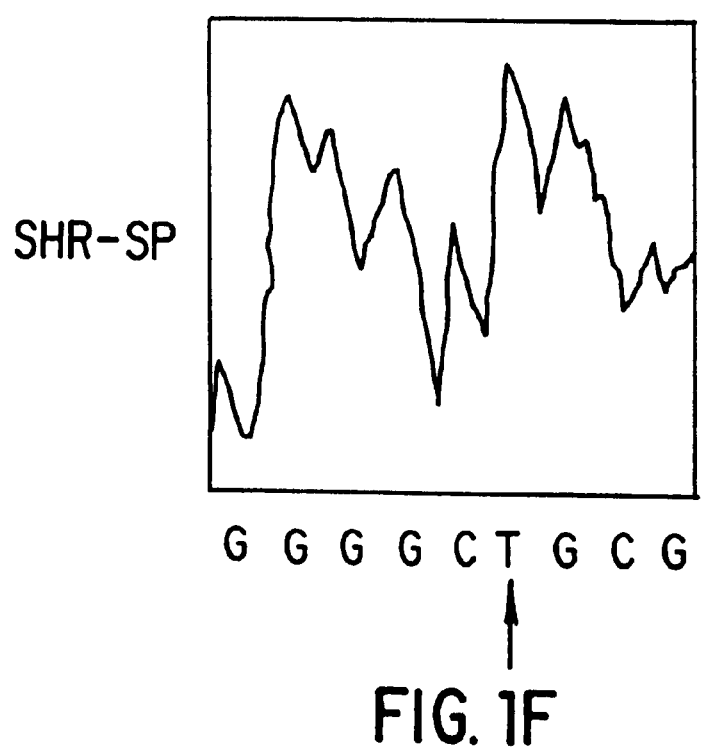

Through the QEA™ analysis, the inventors discovered that ANF was expressed at different levels among these rat strains. The peak representing ANF mRNA was 2-fold more intense in SHRSP and WKY hearts relative to the SHR heart (FIGS. 1A and B). Oligonucleotide poisoning confirmed that the entire magnitude of the intensity peak associated with the ANF transcript was due to amplification of the ANF gene (FIGS. 1C and D).

Comparison of the ANF sequences from SHRSP and SHR rats revealed 9 nucleotide differences, indicating that the SHRSP ANF allele was most likely derived from a foreign rat inadvertently introduced into the colony. One nucleotide substitution changed the glycine at position 99 of proANP as depicted in FIG. 3 (SEQ ID NO:2) to a serine residue (FIGS. 1E and F) (a G to A change at nucleotide number 1125 as depicted in FIG. 4 (SEQ ID NO:3)) and most likely accounts for the protective effect of the allele. This glycine residue is conserved among rat, pig, horse and human and may affect proANP processing and/or the binding of ANF to its receptor. Four variants in the third (i.e. the variant or wobble positions of the codon) positions of the nucleotide sequences coding for the valine at amino acid 27 (an A to G change at nucleotide number 805 as depicted in FIG. 4 (SEQ ID NO:3)), the proline at amino acid 59 (a G to A change at nucleotide number 1007 as depicted in FIG. 4 (SEQ ID NO:3)), the alanine at position 71 (a G to A change at nucleotide number 1043 as depicted in FIG. 4 (SEQ ID NO:3)), and the glutamate at position 85 (an A to G change at nucleotide number 1085 as depicted in FIG. 4 (SEQ ID NO:3)) and 4 variants in the 3' untranslated region (a C to T change and a T to C change at nucleotide numbers 1866 and 1868, respectively, as depicted in FIG. 4 (SEQ ID NO:3) and a two basepair deletion), of SHRSP-Anf do not affect the predicted protein sequence.

The discovery of both a 2-fold increase in mRNA, as well as a protein-altering mutation in ANF in a protective role for stroke onset suggests the mutant protein as a potential therapeutic for stroke.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publication are cited herein, the disclosures of which are incorporated by reference in their entireties.

What is claimed is:

1. A purified polypeptide comprising an amino acid sequence at least 80% identical to SEQ ID NO:2, provided that an amino acid residue in said polypeptide at an amino acid analogous to position 99 of SEQ ID NO:2 is other than glycine.

2. The polypeptide of claim 1, wherein said residue is a substrate for a kinase activity.

3. The polypeptide of claim 1, wherein said residue is serine.

4. The polypeptide of claim 1, wherein said polypeptide comprises an amino acid sequence at least 90% identical to SEQ ID NO:2.

5. The polypeptide of claim 1, said polypeptide further comprising one or more amino acid substitutions at positions analogous to amino acids 100–108 of SEQ ID NO:2.

6. The polypeptide of claim 1, wherein said polypeptide consists of an amino acid sequence having a glycine to serine substitution at amino acid 99 in the amino acid sequence of SEQ ID NO:2.

7. A composition comprising the polypeptide of claim 1 and a pharmaceutically acceptable carrier.

8. A purified polypeptide comprising a mutant amino acid sequence of SEQ ID NO:2, wherein said polypeptide comprises one or more amino acid substitutions at amino acid positions corresponding to residues 99–108 of SEQ ID NO:2, provided that an amino acid residue in said polypeptide at an amino acid corresponding to position 99 of SEQ ID NO:2 is other than glycine.

9. A polypeptide of claim 8, wherein the amino acid residue at position 99 is a serine.

10. A purified polypeptide comprising an amino acid sequence at least 80% identical to SEQ ID NO:5, provided that an amino acid residue in said polypeptide at an amino acid analogous to position 100 of SEQ ID NO:5 is other than glycine.

11. The polypeptide of claim 10, wherein said residue is a substrate for a kinase activity.

12. The polypeptide of claim 11, wherein said residue is serine.

13. The polypeptide of claim 10, wherein said polypeptide comprises an amino acid sequence at least 90% identical to SEQ ID NO:5.

14. The polypeptide of claim 10, said polypeptide further comprising one or more amino acid substitutions at positions analogous to amino acids 101–109 of SEQ ID NO:5.

15. The polypeptide of claim 10, wherein said polypeptide comprises an amino acid sequence having a glycine to serine substitution at amino acid 100 in the amino acid sequence of SEQ ID NO:5.

16. A purified polypeptide comprising a mutant amino acid sequence of SEQ ID NO:5, wherein said polypeptide comprises one or more amino acid substitutions at amino acid positions corresponding to residues 100–109 of SEQ ID NO: 5, provided that an amino acid residue in said polypeptide at an amino acid corresponding to position 100 of SEQ ID NO:5 is other than glycine.

17. A polypeptide of claim 16, wherein the amino acid residue at position 100 is a serine.

18. A composition comprising the polypeptide of claim 10 and a pharmaceutically acceptable carrier.

* * * * *

SEQUENCE LISTING (1) GENERAL INFORMATION:

(iii) NUMBER OF SEQUENCES: 19

(2) INFORMATION FOR SEQ ID NO:1:

(i) SEQUENCE CHARACTERISTICS:
      (A) LENGTH: 28 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:1:

```
Gly Pro Trp Asp Pro Ser Asp Arg Ser Ala Leu Leu Lys Ser Lys Leu
 1               5                  10                  15

Arg Ala Leu Leu Ala Gly Pro Arg Ser Leu Arg Arg
                20                  25
```

(2) INFORMATION FOR SEQ ID NO:2:

(i) SEQUENCE CHARACTERISTICS:
      (A) LENGTH: 152 amino acids
      (B) TYPE: amino acid
      (C) STRANDEDNESS:
      (D) TOPOLOGY: unknown (ii) MOLECULE TYPE: peptide (xi) SEQUENCE DESCRIPTION: SEQ ID NO:2:

```
Met Gly Ser Phe Ser Ile Thr Lys Gly Phe Phe Leu Phe Leu Ala Phe
 1               5                  10                  15

Trp Leu Pro Gly His Ile Gly Ala Asn Pro Val Tyr Ser Ala Val Ser
                20                  25                  30

Asn Thr Asp Leu Met Asp Phe Lys Asn Leu Leu Asp His Leu Glu Glu
                35                  40                  45

Lys Met Pro Val Glu Asp Glu Val Met Pro Pro Gln Ala Leu Ser Glu
    50                  55                  60

Gln Thr Asp Glu Ala Gly Ala Ala Leu Ser Ser Leu Ser Glu Val Pro
65                  70                  75                  80

Pro Trp Thr Gly Glu Val Asn Pro Ser Gln Arg Asp Gly Gly Ala Leu
                85                  90                  95

Gly Arg Gly Pro Trp Asp Pro Ser Asp Arg Ser Ala Leu Leu Lys Ser
                100                 105                 110

Lys Leu Arg Ala Leu Leu Ala Gly Pro Arg Ser Leu Arg Arg Ser Ser
        115                 120                 125

Cys Phe Gly Gly Arg Ile Asp Arg Ile Gly Ala Gln Ser Gly Leu Gly
        130                 135                 140

Cys Asn Ser Phe Arg Tyr Arg Arg
145                 150
```

(2) INFORMATION FOR SEQ ID NO:3:

(i) SEQUENCE CHARACTERISTICS:
        (A) LENGTH: 2360 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

```
GAATTCTTTA GAGCCTGTAT CATGTTGGCT TCCTGGCTGA CTTCATACTC TAAAAAAATA    60

TAATAGCTCT TTCACCTGAC TGCTAACAGG GACATCTAGG GTGGGGTGG GCTGTCTGGG    120

GCCAGAGGTC CACCCACGAG GCCAATGAAT CAGGTGTGAA GGTAACTCCA GTATGCGGGC   180

TCCCCCGCAG CCTAGCTGTC TCCCAGCTGC CTGTCATTGC CTCTCCTCCC GCCCTTATTT   240

GGAGCCCCTG ACAGCTGAGA TGCAAGCAGA GGGAGCTGGG TGTGGGCCAG CCGTCACCCT   300

CTGCTTCCCT GCATGGGTCC CGTTGCCAGG GAGAAGGAAT CCTGAGGCGA GCGCCCAGGA   360

AGATAACCAA GGACTCTTTT CTGCTCTTCT CACACCTTTG AAGTGGGGGC CTCTTGAGGC   420

AAATCATCAA GAATGTGACT CTTGCAGCTG AGGGTCTGGG GGAGGGAGGG TTACTGGAGC   480

TGCTCAAGGC AAAGGGGCTG TGACAAGCTT CGCTGGACTG ATAACTTTAA AAGGGCATCT   540

TCTGCTGGCC GCCGCAAGTG ACAGAATGGG GAGGGTTCCA GCTCTCCTGC GTTCTCAGGG   600

AGCTGGGGGG CTATAAAAAC GGGAGACGCC GGGCAGCTGG GAGACAGTGA CGGACAAAGG   660

CTGAGAGAGA AACCAGAGAG TGAGCCGAGA CAGCAAACAT CAGATCGTGC CCCGACCCAC   720

GCCAGCATGG GCTCCTTCTC CATCACCAAG GGCTTCTTCC TCTTCCTGGC CTTTTGGCTC   780

CCAGGCCATA TTGGAGCAAA TCCCGTATAC AGTGCGGTGT CCAACACAGA TCTGATGGAT   840

TTCAAGGTAG GGCCAGGAAG TGGGGCATGG ACTGGGACCA GGGTCTCCTT GGTACTGGGT   900

CCATTCCTGA GACATCCCCC TTTCTCTGCA TTTATTTTCC CCTGATAAAG AACCTGCTAG   960

ACCACCTGGA GGAGAAGATG CCGGTAGAAG ATGAGGTCAT GCCTCCGCAG GCCCTGAGCG  1020

AGCAGACCGA TGAAGCGGGG GCGGCACTTA GCTCCCTCTC TGAGGTGCCT CCCTGGACTG  1080

GGGAAGTCAA CCCGTCTCAG AGAGATGGAG GTGCTCTCGG GCGCGGCCCC TGGGACCCCT  1140

CCGATAGATC TGCCCTCTTG AAAAGCAAAC TGAGGGCTCT GCTCGCTGGC CCTCGGAGCC  1200

TGCGAAGGTC AAGCTGCTTC GGGGGTAGGA TTGACAGGAT TGGAGCCCAG AGCGGACTAG  1260

GCTGCAACAG CTTCCGGGTA AGAGGCGCTG CGGGTGAAAC GGGATAGAGG CCAGGTGGGG  1320

TCTTGTTAGG GCTCCGACCT TGCCAAGGAC TAGTGCCAGT CTGCATCTTC GGCAGTACAG  1380

AGTCCAGTGC GTGAGTCTTA TGTTCTCTGA GAGTTCTGCC CCACCCTGAT GGGTGTCCCT  1440

TGAGTTTCAA GAGAATGACA GCAGCTGCTG CAGGATCTGA GCCACGAGCA CTGGGAAATT  1500

AGAATACAGG GCCAAGACCG CCCACATTAA CGCTTACCGG CGCCCTGTTT GCCAGTTTAC  1560

CGAAGAGGCC AGACTGTGGC TGGTGGGAAA GAGTTGGTCA CTGGTCAGGT TGAACAGGTT  1620

AGCCCAGTGA AGGTAGATCA TCAGACCGAT TTATTTTTCT CTTTGTAGTA CCGAAGATAA  1680

CAGCCAAATC TGCTCGAGCA GATCGCAAAA GATCCCAAGC CTTGCGGTGT GTCACACAGC  1740

TTGGTCGCAT TGCCACTGAG AGGTGGTGAA TACCCTCCTG GAGCTGCAGC TTCCTGTCTT  1800

CATCTATCAC GATCGATGTT AAGTGTAGAT GAGTGGTTTA GTGAGGCCTT ACCTCTCCCA  1860

CTCTGCATAT TAAGGTAGAT CCTCACCCCT TTCAGAAAGC AGTTGGAAAA AAATAAATCC  1920

GAATAAACTT CAGCACCACG GACAGACGCT GAGGCCTGGC TGCGGTTCTT TGGCTCCTTT  1980

CTGTCACCAG TTCCTTGCGG TCCACAACCT TGATCTTTCG TTTCTCCCTC CTTCCCTCCT  2040
```

```
TCTTCTTGCT GGGCGTGTGT GTGTGTGTGT GTGATGGTGT GTGTGTGTGT GTGTGTGTGT    2100

GTGTGTGTGT GTGTGTGTGT GTGTGTGTGT TGGTGAGGGG GTCACACTAT GGCCCTCAAC    2160

ATGCTCTGCC TCCATTGCAG AACCCTGAAA AGCTCGCCCA GACTGAAAAG GGCATTTATT    2220

TTTAATTACC TTTAAAATAC CTTTTCCTGA GGACAGAGGC AATGATACGT ATGCTTAGTT    2280

TCACGAATCC CTCTCACTGT CTGGCTACAG CCTGGGTGGC TTTAAGGGGC ATTTGAGAGG    2340

ACCAGGGACT ATCCAGATCT                                                 2360
```

(2) INFORMATION FOR SEQ ID NO:4:

(i) SEQUENCE CHARACTERISTICS:
        (A) LENGTH: 28 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:4:

```
Gly Pro Trp Asp Ser Ser Asp Arg Ser Ala Leu Leu Lys Ser Lys Leu
 1               5                  10                  15

Arg Ala Leu Leu Thr Ala Pro Arg Ser Leu Arg Arg
            20                  25
```

(2) INFORMATION FOR SEQ ID NO:5:

(i) SEQUENCE CHARACTERISTICS:
        (A) LENGTH: 151 amino acids
        (B) TYPE: amino acid
        (C) STRANDEDNESS:
        (D) TOPOLOGY: unknown (ii) MOLECULE TYPE: peptide (xi) SEQUENCE DESCRIPTION: SEQ ID NO:5:

```
Met Ser Ser Phe Ser Thr Thr Thr Val Ser Phe Leu Leu Leu Leu Ala
 1               5                  10                  15

Phe Gln Leu Leu Gly Gln Thr Arg Ala Asn Pro Met Tyr Asn Ala Val
            20                  25                  30

Ser Asn Ala Asp Leu Met Asp Phe Lys Asn Leu Leu Asp His Leu Glu
            35                  40                  45

Glu Lys Met Pro Leu Glu Asp Glu Val Val Pro Pro Gln Val Leu Ser
 50                  55                  60

Glu Pro Asn Glu Glu Ala Gly Ala Ala Leu Ser Pro Leu Pro Glu Val
 65                  70                  75                  80

Pro Pro Trp Thr Gly Glu Val Ser Pro Ala Gln Arg Asp Gly Gly Ala
            85                  90                  95

Leu Gly Arg Gly Pro Trp Asp Ser Ser Asp Arg Ser Ala Leu Leu Lys
            100                 105                 110

Ser Lys Leu Arg Ala Leu Leu Thr Ala Pro Arg Ser Leu Arg Arg Ser
            115                 120                 125

Ser Cys Phe Gly Gly Arg Met Asp Arg Ile Gly Ala Gln Ser Gly Leu
            130                 135                 140

Gly Cys Asn Ser Phe Arg Tyr
145                 150
```

(2) INFORMATION FOR SEQ ID NO:6:

(i) SEQUENCE CHARACTERISTICS:
        (A) LENGTH: 845 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

```
TGGCGAGGGA CAGACGTAGG CCAAGAGAGG GGAACCAGAG AGGAACCAGA GGGGAGAGAC     60
AGAGCAGCAA GCAGTGGATT GCTCCTTGAC GACGCCAGCA TGAGCTCCTT CTCCACCACC    120
ACCGTGAGCT TCCTCCTTTT ACTGGCATTC CAGCTCCTAG GTCAGACCAG AGCTAATCCC    180
ATGTACAATG CCGTGTCCAA CGCAGACCTG ATGGATTTCA AGAATTTGCT GGACCATTTG    240
GAAGAAAAGA TGCCTTTAGA AGATGAGGTC GTGCCCCCAC AAGTGCTCAG TGAGCCGAAT    300
GAAGAAGCGG GGGCTGCTCT CAGCCCCCTC CCTGAGGTGC CTCCCTGGAC CGGGGAAGTC    360
AGCCCAGCCC AGAGAGATGG AGGTGCCCTC GGGCGGGGCC CCTGGGACTC CTCTGATCGA    420
TCTGCCCTCC TAAAAAGCAA GCTGAGGGCG CTGCTCACTG CCCCTCGGAG CCTGCGGAGA    480
TCCAGCTGCT TCGGGGGCAG GATGGACAGG ATTGGAGCCC AGAGCGGACT GGGCTGTAAC    540
AGCTTCCGGT ACTGAAGATA ACAGCCAGGG AGGACAAGCA GGGCTGGGCC TAGGGACAGA    600
CTGCAAGAGG CTCCTGTCCC CTGGGGTCTC TGCTGCATTT GTGTCATCTT GTTGCCATGG    660
AGTTGTGATC ATCCCATCTA AGCTGCAGCT TCCTGTCAAC ACTTCTCACA TCTTATGCTA    720
ACTGTAGATA AAGTGGTTTG ATGGTGACTT CCTCGCCTCT CCCACCCCAT GCATTAAATT    780
TTAAGGTAGA ACCTCACCTG TTACTGAAAG TGGTTTGAAA GTGAATAAAC TTCAGCACCA    840
TGGAC                                                              845
```

(2) INFORMATION FOR SEQ ID NO:7:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

```
GAATTCAGTT CTCTCCTTCC GCT                                           23
```

(2) INFORMATION FOR SEQ ID NO:8:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

```
CATGCTGGCG TGGGACGGGG CAC                                           23
```

(2) INFORMATION FOR SEQ ID NO:9:

(i) SEQUENCE CHARACTERISTICS:
        (A) LENGTH: 21 base pairs
        (B) TYPE: nucleic acid (C) STRANDEDNESS: single
        (D) TOPOLOGY: linear (ii) MOLECULE TYPE: DNA (xi) SEQUENCE DESCRIPTION: SEQ ID NO:9:

GGATCCATTT GTCTCGGGCT G                                            21

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

CTAGATCAAT TAGGCCTCCC                                              20

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

AGATGGAGGT GCTCTCGGGC GCA                                          23

(2) INFORMATION FOR SEQ ID NO:12:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

AGATGGAGGT GCTCTCGGGC GCG                                          23

(2) INFORMATION FOR SEQ ID NO:13:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

AGAGATGGAG GTGCCCTCGG GCGGA                                        25

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:14:

AGAGATGGAG GTGCCCTCGG GCGGG                                              25

(2) INFORMATION FOR SEQ ID NO:15:

(i) SEQUENCE CHARACTERISTICS:
            (A) LENGTH: 13 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:15:

GGCCCGAAGT ACA                                                           13

(2) INFORMATION FOR SEQ ID NO:16:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:16:

GGCCCGAAGT AC                                                            12

(2) INFORMATION FOR SEQ ID NO:17:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:17:

GGCCCAGCCA CT                                                            12

(2) INFORMATION FOR SEQ ID NO:18:

(i) SEQUENCE CHARACTERISTICS:
            (A) LENGTH: 11 base pairs
            (B) TYPE: nucleic acid
            (C) STRANDEDNESS: single
            (D) TOPOLOGY: linear (ii) MOLECULE TYPE: DNA (xi) SEQUENCE DESCRIPTION: SEQ ID NO:18:

GGCCCAGCCA C                                                             11

(2) INFORMATION FOR SEQ ID NO:19:

(i) SEQUENCE CHARACTERISTICS:
            (A) LENGTH: 16 base pairs
            (B) TYPE: nucleic acid
            (C) STRANDEDNESS: single
            (D) TOPOLOGY: linear -continued (ii) MOLECULE TYPE: DNA (xi) SEQUENCE DESCRIPTION: SEQ ID NO:19:

AAGATGCCGG TAGAAG                                                    16